US007347824B2

(12) United States Patent
Wilkinson et al.

(10) Patent No.: US 7,347,824 B2
(45) Date of Patent: Mar. 25, 2008

(54) METHOD AND APPARATUS FOR DETERMINING CONDITIONS OF BIOLOGICAL TISSUES

(75) Inventors: Malcolm Howard Wilkinson, Forest Hill (AU); Clive Andrew Ramsden, Cheltenham (AU); Philip John Berger, Carlton (AU)

(73) Assignee: Pulmosonix Pty Ltd., Armadale, Victoria (AU)

( * ) Notice: Subject to any disclaimer, the term of this patent is extended or adjusted under 35 U.S.C. 154(b) by 1026 days.

(21) Appl. No.: 10/272,494

(22) Filed: Oct. 15, 2002

(65) Prior Publication Data

US 2003/0120182 A1 Jun. 26, 2003

Related U.S. Application Data

(63) Continuation of application No. PCT/AU01/00465, filed on Apr. 20, 2001.

(30) Foreign Application Priority Data

Apr. 20, 2000 (AU) .................... PQ7040
Apr. 10, 2001 (AU) .................... PR4333

(51) Int. Cl.
*A61B 5/08* (2006.01)
(52) U.S. Cl. ................... 600/529; 600/533
(58) Field of Classification Search ........... 600/533
See application file for complete search history.

(56) References Cited

U.S. PATENT DOCUMENTS

| 3,990,435 A | 11/1976 | Murphy |
| 4,094,304 A | 6/1978 | Wright |
| 4,197,856 A | 4/1980 | Northrop |
| 4,326,416 A | 4/1982 | Fredberg |
| 4,672,977 A | 6/1987 | Kroll |

(Continued)

FOREIGN PATENT DOCUMENTS

FR 2672793 A1 2/1991

(Continued)

OTHER PUBLICATIONS

Dalmay et al. "Acoustic Properties of the Normal Chest" *European Respiratory Journal* (1995) vol. 8, pp. 1761-1769.

(Continued)

*Primary Examiner*—Charles A. Marmor, II
*Assistant Examiner*—Patricia C Mallari
(74) *Attorney, Agent, or Firm*—Ladas and Parry LLP

(57) ABSTRACT

The present invention relates to a method of determining characteristics of biological tissues in humans and animals. In particular, it relates to determining the characteristics of tissues such as the lungs and airways by introducing a sound to the tissue, and recording the sound. The invention further includes an apparatus capable of such measurement. In a first aspect of the present invention there is provided a method of determining characteristics of biological tissue in situ, including: introducing a sound to the tissue at first position; detecting the sound at another position spaced from the first position after it has traveled through the tissue; calculating the velocity and attenuation of sound that has traveled through the tissue from the first position to another position; and correlating the velocity and attenuation of the detected sound to characteristics of the biological tissue.

18 Claims, 13 Drawing Sheets

U.S. PATENT DOCUMENTS

| | | | | |
|---|---|---|---|---|
| 4,830,015 | A | 5/1989 | Okazaki | 128/660.06 |
| 4,982,738 | A | 1/1991 | Griebel | |
| 5,165,417 | A | 11/1992 | Murphy, Jr. | 128/716 |
| 5,239,997 | A * | 8/1993 | Guarino et al. | 600/587 |
| 5,259,373 | A | 11/1993 | Gruenke et al. | |
| 5,311,875 | A | 5/1994 | Stasz | |
| 5,316,002 | A | 5/1994 | Jackson et al. | |
| 5,361,767 | A | 11/1994 | Yukov | 128/660.06 |
| 5,417,215 | A | 5/1995 | Evans et al. | 128/660.06 |
| 5,485,841 | A | 1/1996 | Watkin et al. | 128/660.01 |
| 5,588,439 | A | 12/1996 | Hollub | |
| 5,666,960 | A | 9/1997 | Fredberg et al. | |
| 5,746,699 | A | 5/1998 | Fredberg et al. | |
| 5,844,997 | A | 12/1998 | Murphy | 381/92 |
| 5,882,314 | A | 3/1999 | Fredberg et al. | |
| 5,919,139 | A | 7/1999 | Lin | 600/443 |
| 6,045,514 | A | 4/2000 | Raviv et al. | |
| 6,139,505 | A | 10/2000 | Murphy | 600/532 |
| 6,213,955 | B1 | 4/2001 | Karakasoglu et al. | |
| 6,241,683 | B1 | 6/2001 | Macklem et al. | |
| 6,261,238 | B1 | 7/2001 | Gavriely | |
| 6,383,142 | B1 | 5/2002 | Gavriely | |
| 6,394,967 | B1 | 5/2002 | Murphy | 600/586 |
| 6,440,083 | B1 | 8/2002 | Fredberg et al. | |
| 6,443,907 | B1 | 9/2002 | Mansy et al. | |
| 6,454,724 | B1 | 9/2002 | Greene | |
| 6,491,641 | B1 | 12/2002 | Rasmussen | |
| 6,517,497 | B2 | 2/2003 | Rymut et al. | |
| 6,595,928 | B2 * | 7/2003 | Mansy et al. | 600/529 |
| 6,811,538 | B2 | 11/2004 | Westbrook et al. | |
| 2002/0014235 | A1 | 2/2002 | Rogers et al. | |
| 2002/0072685 | A1 | 6/2002 | Rymut et al. | |
| 2002/0183642 | A1 | 12/2002 | Murphy | 600/532 |
| 2002/0193697 | A1 | 12/2002 | Cho et al. | |
| 2003/0045806 | A1 | 3/2003 | Brydon | |
| 2004/0010202 | A1 | 1/2004 | Nakatani et al. | |
| 2004/0059240 | A1 | 3/2004 | Cho et al. | |
| 2004/0069304 | A1 | 4/2004 | Jam | |
| 2004/0236241 | A1 | 11/2004 | Murphy | |
| 2004/0254493 | A1 | 12/2004 | Chervin et al. | |
| 2005/0005935 | A1 | 1/2005 | Gradon | |
| 2005/0020932 | A1 | 1/2005 | Haberland et al. | |
| 2005/0027207 | A1 | 2/2005 | Westbrook et al. | |
| 2005/0043645 | A1 | 2/2005 | Ono et al. | |

FOREIGN PATENT DOCUMENTS

| | | |
|---|---|---|
| FR | 2 672 793 | 8/1992 |
| FR | 2672793 | 8/1992 |
| WO | 9932035 | 7/1999 |
| WO | 00/33735 | 6/2000 |
| WO | 02/13677 | 2/2002 |
| WO | 02/13697 | 2/2002 |
| WO | 02/43579 | 6/2002 |
| WO | 02/065901 | 8/2002 |
| WO | 03/024335 | 3/2003 |
| WO | 03/061471 | 7/2003 |
| WO | 03/063701 | 8/2003 |
| WO | 03/075739 | 9/2003 |
| WO | 03/092493 | 11/2003 |

OTHER PUBLICATIONS

Pasterkamp et al. "Respiratory Sounds-Advances Beyond the Stethoscope" *American Journal of Respiratory and Critical Care Medicine* (1997) vol. 156, pp. 975-985.
Karnath et al. "Pulmonary Auscultation" *Hospital Physician* (2002) pp. 22-26.
Leung et al. "Sound Transmission Between 50 and 600 Hz in Excised Pig Lungs Filled with Air and Helium" *Journal of Applied Physiology* (2000) vol. 89, Issue 6, pp. 2472-2482.
Wodicka et al. "Spectral Characteristics of Sound Transmission in the Human Respiratory System" *IEEE Transactions on Biomedical Engineering* (1990) vol. 37, No. 12, pp. 1130-1135.
Leung et al. "Sound Transmission Through Normal and Diseased Human Lungs" *Engineering Science and Education Journal* (1996) pp. 25-31.
Wodicka et al. "Phase Delay of Pulmonary Acoustic Transmission from Trachea to Chest Wall" *IEEE Transactions on Biomedical Engineering* (1992) vol. 39, No. 10, pp. 1053-1059.
Mahagnah et al. "Gas Density Does Not Affect Pulmonary Acoustic Transmission in Normal Men" *Journal of Applied Physiology* (1995) vol. 78, Issue 3, pp. 928-937.
Pohlmann et al. "Effect of Changes in Lung Volume on Acoustic Transmission through the Human Respiratory System" *Physiological Measurement* (2001) vol. 22, pp. 233-243.
Huang et al. "A New Nasal Acoustic Reflection Technique to Estimate Pharyngeal Cross-Sectional Area During Sleep" *Journal of Applied Physiology* (2000) vol. 88, pp. 1457-1466.
Poort et al. "Airway Area by Acoustic Reflection: A Corrected Derivation for the Two-Microphone Method" *Journal of Biomechanical Engineering* (1999) vol. 121, pp. 663-665.
Marshall et al. "Acoustic Reflectometry for Airway Measurements in Man: Implementation and Validation" *Physiological Measurement* (1993) vol. 14, pp. 157-169.
Louis et al. "Airway Area by Acoustic Reflection: The Two-Microphone Method" *Journal of Biomechanical Engineering* (1993) vol. 115, pp. 278-285.
Rubinstein et al. "Effect of Mouthpiece, Noseclips, and Head Position on Airway Area Measured by Acoustic Reflections" *The American Physiological Society* (1987) pp. 1469-1474.
Brooks et al. "Reproducibility and Accuracy of Airway Area by Acoustic Reflection" *Journal of Applied Physiology* (1986) vol. 57, pp. 777-787.
Fredberg et al. "Airway Area by Acoustic Reflections Measured at the Mouth" *Journal of Applied Physiology* (1980) vol. 48, pp. 749-758.
Sidell et al. "Noninvasive Inference of Airway Network Geometry from Broadband Lung Reflection Data" *Journal of Biomechanical Engineering* (1978) vol. 100, pp. 131-138.
Jackson et al. "Airway Geometry by Analysis of Acoustic Pulse Response Measurements" *Journal of Applied Physiology* (1977) vol. 43, pp. 523-536.
Ware et al. "Continuous and Discrete Inverse-Scattering Problems in a Stratified Elastic Medium-I. Plane Waves at Normal Incidence" *The Journal of Acoustical Society of America* (1969) vol. 45, No. 4, pp. 911-921.
Faber et al. "Flextube Reflectometry for Localization of Upper Airway Narrowing-A Preliminary Study in Models and Awake Subjects" *Respiratory Medicine* (2001) vol. 95, pp. 631-638.
Carrive et al. "Biophony: An Open System to Measure the Airway Area by Acoustic Reflection" *18th Annual International Conference of the IEEE Engineering in Medicine and Biology Society* (1996) pp. 125-126.
Murphy et al. "Spectral Characteristics of Lung Sounds in Patients with Chronic Obstructive Lung Disease" *Faulkner Hospital*, Boston, MA, presented at ATS 2004 (2002) one page.
Murphy et al. "Inhomogeneity of the Timing of Lung Sounds in Patients with Chronic Obstructive Lung Disease" *Faulkner Hospital*, Boston, MA, presented at ATS 2002 (2002) one page.
Murphy et al."Lung Sound Patterns in Common Pulmonary Disorders" *Faulkner Hospital*, Boston, MA, presented at ATS 2002 (2002) one page.
Derwent English Abstract of FR 2672793 Dated Aug. 21, 1992.
Murphy R et al., *Sound speed in the lung measured by sound injection into supraclavicular space.*, Presented at the European Respiratory Society Congress (Stockholm, Sweden), (Sep. 15, 2002) abstract.
Paciej R et al., *Transpulmonary speed of sound input into supraclavicular space*, J. Appl. Physiol, vol. 94 (2003) pp. 604-611.
Bergstresser T et al., *Sound transmission in the lung as a function of lung volume*, J. Appl. Physiol. vol. 93 (2002) pp. 667-674.

* cited by examiner

Fig 1. Pressure-volume curve of a moderately diseased lung illustrating two hazards of lung volume with an optimal "safe" window between (from Froese, 1997).

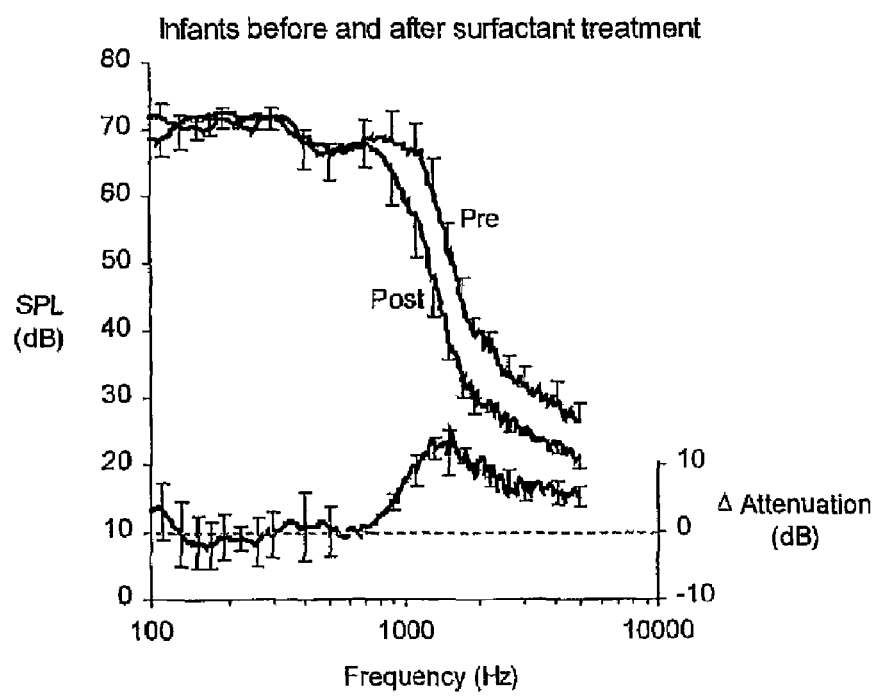
Figure 5(a)
Figure 5(b)
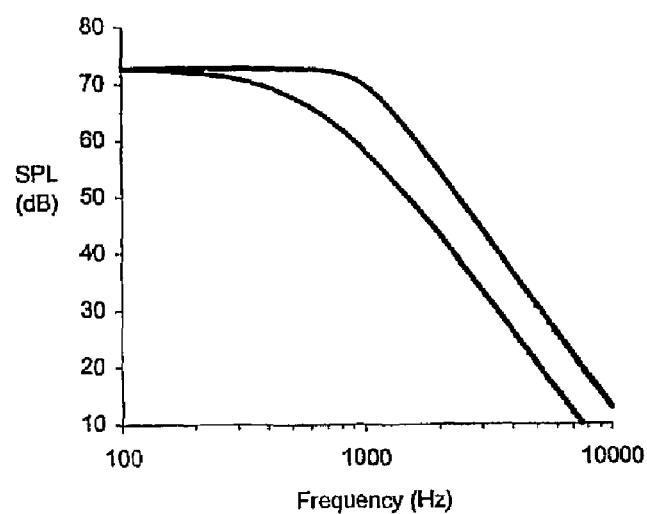

METHOD AND APPARATUS FOR DETERMINING CONDITIONS OF BIOLOGICAL TISSUES

This application is a continuation of copending International Application PCT/AU01/0046-5 filed on 20 Apr. 2001, which designated the U.S., claims the benefit thereof and incorporates the same by reference.

The present invention relates to a method of determining characteristics of biological tissues in humans and animals. In particular, it relates to determining the characteristics of tissues such as the lungs and airways by introducing a sound to the tissue, and recording the sound. The invention further includes an apparatus capable of such measurement.

BACKGROUND OF THE INVENTION

Non-invasive determination of the condition of biological tissues is useful in particular where the patient is unable to co-operate or the tissue is inaccessible for easy monitoring.

Techniques presently used in determining the characteristics of biological tissues include x-rays, magnetic resonance imaging (MRI) and radio-isotopic imaging. These are generally expensive and involve some degree of risk which is usually associated with the use of X-rays, radioactive materials or gamma-ray emission. Furthermore, these techniques are generally complicated and require equipment which is bulky and expensive to install and, in most cases, cannot be taken to the bedside to assess biological tissues in patients whose illness prevents them being moved. The present invention provides a method which alleviates these difficulties, providing a non-invasive, cost-effective and ambulatory means for assessing and monitoring the condition of biological tissues in humans and animals alike.

Sound waves, particularly in the ultra-sound range have been used to monitor and observe the condition of patients or of selected tissues, such as the placenta or fetus. However, the process requires sophisticated and sometimes expensive technology and cannot be used in tissues in which there is a substantial quantity of gas, such as the lung.

Every year in Australia about 5000 newborn infants require a period of intensive care (ANZNN Annual Report, 1996-1997). Respiratory failure is the most common problem requiring support and is usually treated with a period of mechanical ventilation. Over the last decade the mortality of infants suffering respiratory failure has shown an impressive decline, attributable at least in part to improved techniques used in mechanical ventilation, and the introduction of surfactant replacement therapy (Jobe, 1993). The vast majority of infants now survive initial acute respiratory illness, but lung injury associated with mechanical ventilation causes many infants to develop 'chronic lung disease'. Chronic lung disease is characterised by persisting inflammatory and fibrotic changes, and causes over 90% of surviving infants born at less than 28 weeks gestation, and 30% of those of 28-31 weeks gestation, to be dependent on supplementary oxygen at 28 days of age. Of these, over half still require supplementary oxygen when they have reached a post-menstrual age of 36 weeks gestation (ANZNN Annual report, 1996-1997). Assistance with continuous positive airway pressure (CPAP) or artificial ventilation is also commonly required.

Historically, barotrauma and oxygen toxicity have been considered to be the primary culprits in the aetiology of chronic lung disease (Northway et al, 1967; Taghizadeh & Reynolds, 1976). However, trials of new strategies in mechanical ventilation which were expected to reduce barotrauma and/or exposure to oxygen have often had disappointingly little impact on the incidence of chronic lung disease (HIFI Study Group, 1989; Bernstein et al, 1996; Baumer, 2000). Comparison of strategies of conventional mechanical ventilation in animals (Dreyfuss et al, 1985) have indicated that high lung volumes may be more damaging than high intrapulmonary pressures, and has led to the concept of 'volutrauma' due to over-inflation of the lung. At the same time, experience with high frequency oscillatory ventilation (HFOV) has indicated that avoidance of under-inflation may be equally important. HFOV offers the potential to reduce lung injury by employing exceptionally small tidal volumes which are delivered at a very high frequency. However, this technique fails to confer benefit, if the average lung volume is low (HIFI Study Group, 1989), yet it appears to be successful if a normal volume is maintained (McCulloch et al, 1988; Gerstmann et al, 1996). This highlights the importance of keeping the atelectasis-prone lung 'open' (Froese, 1989). Evidence of this kind has led to the concept that a 'safe window' of lung volume exists within which the likelihood of lung injury can be minimised. The key to preventing lung injury may lie in maintaining lung volume within that safe window thereby avoiding either repetitive over-inflation or sustained atelectasis. (See FIG. 1).

Attempts to maintain an optimal lung volume in the clinical setting are frustrated by a lack of suitable methods by which the degree of lung inflation can be monitored. In current practice, evaluation of oxygen requirements and radiological examination of the lungs are the principal techniques employed. However, oxygen requirements may be influenced by factors other than lung volume (for example intra- or extracardiac right to left shunting), and the hazards of radiation exposure prevent radiological examination being performed with the frequency required.

Monitoring of infants during mechanical ventilation has been significantly improved over the last decade by the incorporation of a pneumotachograph or hot-wire anemometer into the design of many neonatal ventilators. Although this provides a valuable tool for monitoring tidal volume and compliance, it gives only the most indirect indication (from the shape of the pressure-volume curve) of whether that tidal volume is being delivered in a setting of under-inflation, optimal inflation, or over-inflation. Furthermore, while absolute lung gas volume can be measured using 'gold-standard' techniques of Nitrogen ($N_2$) washout or Helium (He) dilution, these are impractical for routine clinical use.

Even when lung volume is maintained in the "safe window", changes in the lung condition may manifest due to the general damaged or underdeveloped condition of the lung. Fluid and blood may accumulate in the lung, posing additional threats to the patient. Evaluation with a stethoscope of audible sounds which originate from within the lung (breath sounds) or are introduced into the lung (by percussion, or as vocal sounds) forms an essential part of any routine medical examination. However, in the sick newborn, the infant's small size, inability to co-operate and the presence of background noise greatly limits the value of such techniques.

Whilst determining and monitoring lung condition in newborn babies is difficult, determining lung condition in adults can be equally as challenging, particularly if a patient is unconscious or unable to cooperate. This places a further limitation on the presently available techniques for monitoring lung condition. Therefore, a clear need exists for a simple, non-invasive and convenient method by which the condition of the lung can be closely monitored in the clinical setting. Similarly, there is a need for a simple, non-invasive and convenient method of determining the condition of other biological tissues which may be prone to changes in their characteristics, through pathology or otherwise.

Accordingly, the present invention overcomes or at least alleviates some of the problems of the prior art.

SUMMARY OF THE INVENTION

In a first aspect of the present invention there is provided a method of determining characteristics of biological tissue in situ, including:

introducing a sound to the tissue at a first position;
detecting the sound at a second position spaced from the first position after it has traveled through the tissue;
calculating the velocity and attenuation of sound that has traveled through the tissue from the first position to the second position; and
correlating the velocity and attenuation of the detected sound to characteristics of the biological tissue.

In another aspect of the present invention there is provided an apparatus for determining characteristics of biological tissues, the apparatus including:

a sound generating device which generates an audible sound;
a recording device which records the sound after it has traveled from one position of the biological tissue, through the tissue and to another position of the tissue;
an analysis device which calculates the velocity with which the sound travels through the tissue, and its attenuation, and which can preferably perform spectral analysis on the data recorded.

In an embodiment of the invention, a characteristic being determined is a state of the upper airways in a respiratory tract in a patient in situ, wherein:

the first position is in the upper airways;
the sound is detected after it has traveled through the upper airways;
the calculated velocity and attenuation is of the sound that has traveled through the upper airways; and
the velocity and attenuation of the sound is correlated to a characteristic being the state of the upper airways.

This method is particularly useful for monitoring for sleep apnoea.

In a preferred aspect of the present invention of the characteristics are determined for monitoring lung condition in situ and wherein:

the audible sound is introduced transthoracically so that the sound travels from the first position on one side of the thorax, through the lung, to the second position on another side of the thorax;
the calculating step includes measuring the velocity and attenuation of the sound as it travels from one side of the thorax, through and across the lung, to the other side of the thorax; and
the attenuation, the sound velocity and velocity dispersion are correlated to a characteristic being lung condition.

Previous work shows that measurement of sound velocity alone may provide a technique for assessing lung density and gives an insight into the degree of lung inflation. However, no attempt has been made to evaluate the potential utility of the measurement of sound velocity and attenuation as a clinical tool.

In yet another preferred aspect of the present invention the characteristics are determined for measuring lung inflation, wherein:

the audible sound is introduced transthoracically so that the sound travels from the first position on one side of the thorax, through the lung, to the second position on another side of the thorax;
the calculating step includes measuring the velocity and attenuation of the sound as it travels from one side of the thorax, through and across the lung, to the other side of the thorax; and
changes in sound velocity and attenuation are correlated with characteristics being lung volume and inflation.

In yet another preferred aspect of the present invention, of the characteristics are determined for predicting chronic lung disease in infants, wherein:

the audible sound is introduced transthoracically so that the sound travels from the first position on one side of the thorax, through the lung, to the second position on another side of the thorax;
the calculating step includes measuring the velocity and attenuation of the sound as it travels from one side of the thorax, through and across the lung, to the other side of the thorax; and
the correlating step includes comparing and the measured sound velocity and attenuation with that of a normal lung in the absence of chronic lung disease.

In yet another preferred aspect of the invention of the characteristics are determined for diagnosing lung disease, said method including measuring lung density, wherein:

the audible sound is introduced transthoracically so that the sound travels from the first position on one side of the thorax, through the lung, to the second position on another side of the thorax;
the calculating step includes measuring the velocity and attenuation of the sound as it travels from one side of the thorax, through and across the lung, to the other side of the thorax; and
the correlating step includes correlating sound velocity and attenuation with lung density and comparing the density of the lung being diagnosed with the density of a normal lung to determine if the lung being diagnosed is diseased.

In yet another preferred aspect of the present invention, the characteristics are determined for preventing lung injury, said method including monitoring lung condition, wherein:

the audible sound is introduced transthoracically so that the sound travels from the first position on one side of the thorax, through the lung, to the second position on another side of the thorax;
the calculating step includes measuring the velocity and attenuation of the sound as it travels from one side of the thorax, through and across the lung, to the other side of the thorax;
the correlating step includes correlating the sound velocity and attenuation with a characteristic being lung volume; and the method further includes the step of:
maintaining a lung volume at an optimal volume such that the lung is substantially free of atelectasis or over-inflation (volutrauma).

In yet another preferred aspect of the present invention, there is provided an apparatus for monitoring lung condition, said apparatus including:

a sound generating means to generate an audible sound transthoracically so that the sound travels from one side of the thorax, through the lung, to another side of the thorax;
a recording means to record the sound after it has traveled from one side of the thorax, through and across the lung, to the other side of the thorax;

an analysis device which calculates the attenuation and velocity with which the sound travels from one side of the thorax, through and across the lung, to the other side of the thorax, and which can preferably perform spectral analysis on the data recorded.

BRIEF DESCRIPTION OF THE FIGURES

FIG. 5(a) shows the SPL measured at a chest microphone, recorded before (pre) and after (post) administration of surfactant in 3 preterm infants, wherein the sound level produced by the transducer was 105 dB (Sheridan 2000). FIG. 5(b) shows the electric model simulation of FIG. 5(a), demonstrating the change in the SPL measured at the chest wall following a 3-fold increase in lung gas compliance, wherein the sound level produced by the transducer was, again, dB.

DETAILED DESCRIPTION

Figure 7:
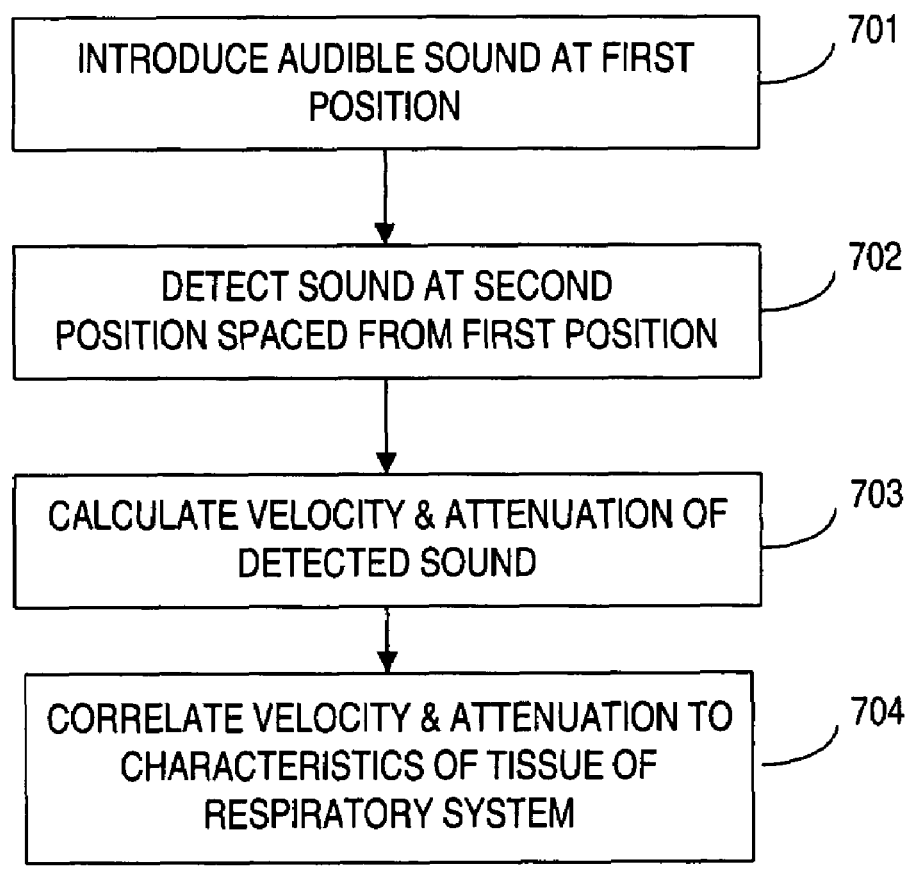
FIG. 7 shows the steps of a method of determining characteristics of tissue of the respiratory system.

In a first aspect of the present invention there is provided a method of determining characteristics of biological tissue in situ, said method illustrated in FIG. 7 and including:

in a step 701, introducing an audible sound to the tissue at a first position;

in a step 702, detecting the sound at another a second spaced from the first position after it has traveled through the tissue;

in a step 703, calculating the velocity and attenuation of sound that has traveled through the tissue from the first position to the second position; and in a step 704, correlating the velocity and attenuation of the detected sound to characteristics of the biological tissue.

Characteristics of biological tissues can be determined by measuring the velocity and attenuation of a sound as it propagates through the tissue. This can be achieved by introducing a sound to a particular location or position on the tissue, allowing the sound to propagate through the tissue and measuring the velocity and attenuation with which the sound travels from its source to its destination, wherein the destination includes a receiver which is spatially separated from the sound's source.

Characteristics of the biological tissue may include a feature of the tissue including but limited to its make-up, volume, condition or position in the body.

Biological tissues may include any single tissue or a group of tissues making up an organ or part or region of the body. The tissue may comprise a homogeneous cellular material or it may be a composite structure such as that found in regions of the body including the thorax which for instance can include lung tissue, gas, skeletal tissue and muscle tissue. However, it is particularly preferred that the tissue is porous which comprises a composite structure made up of tissue and gas or has regions of high and low density such as that found in bone tissue.

Preferably the tissue is of the respiratory system. More preferably the tissue is lung tissue or from the upper airway of the respiratory system. Preferably the upper airway includes the buccal region extending to the trachea before entering the lungs.

Throughout the description and claims of this specification, the word "comprise" and variations of the word, such as "comprising" and "comprises", is not intended to exclude other additives, components, integers or steps.

An understanding of the theoretical aspects of sound transmission in tissue is essential for the best use of bio-acoustic data which is obtained using the present invention.

A unique feature of sound propagation through the lung parenchyma is that the sound velocity is less than that expected for either tissue (1500 ms$^{-1}$) or air (343 ms$^{-1}$). This can be explained, in part, by examining the basic relationship between sound velocity v and the physical properties of the lung tissue through which the sound is propagating. This relationship is: —

$$v = \frac{1}{\sqrt{\rho C}} \quad (1)$$

where ρ is the density and C is the volumetric compliance or inverse volumetric stiffness per unit volume. In determining the velocity of sound in air, substituting an air density of 1.2 kgm$^{-3}$ and an air compliance of 7.14×10$^{-6}$ Pa$^{-1}$ yields a sound velocity in air of 342 ms$^{-1}$.

Rice(1983) has shown that this relationship also holds for composite porous materials with a closed cell structure which is similar to that of the lung, but where ρ and C are replaced by the tissue's average or composite values.

Expressing these values in terms of the volumetric fraction of tissue h and of gas (1−h) and the constituent densities and compliances gives tissue density:

$$\rho = (1-h)\rho_g + h\rho_t \quad (2)$$

and volumetric compliance:

$$C = (1-h)C_g + hC_t \quad (3)$$

where $\rho$, $\rho_g$, $\rho_t$ are the composite, gas and tissue densities respectively and C, $C_g$, $C_t$ are the composite, gas and tissue volumetric compliances respectively.

Substituting equations (2) and (3) into equation (1) yields an expression which relates sound velocity through a composite structure to the volumetric fraction and the physical properties of both the tissue and gas which compose the material:

$$v = \frac{1}{\sqrt{((1-h)\rho_g + h\rho_t)((1-h)C_g + hC_t)}} \quad (4)$$

It must also be noted that the density of air is approximately 3 orders of magnitude less than that of most tissues and the volumetric compliance of air is some 4 orders of magnitude larger than that of most tissues. This can be used to determine the velocity of sound propagation through the lung for a range of volumetric fractions which are likely to be seen in the lung, (0.05 at TLC to 0.5 to 0.9 for a fully atelectatic/collapsed lung). These velocities can be determined by simplifying equation 4 as follows:

$$v = \frac{1}{\sqrt{h(1-h)}} \frac{1}{\sqrt{\rho_t C_g}} \quad (5)$$

Figure 3:
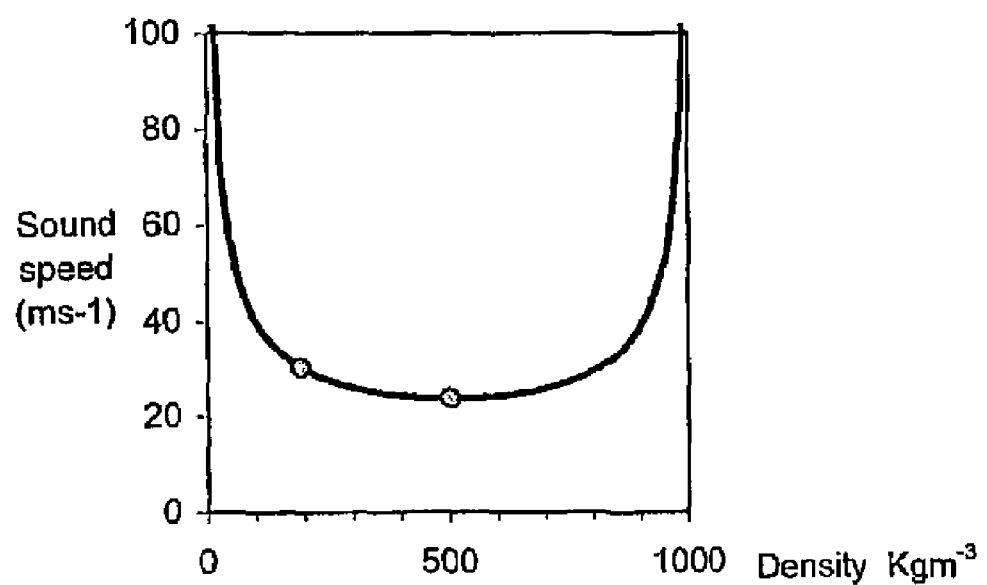
FIG. 3 illustrates the relationship between sound velocity and the volumetric fraction of tissue h and the average lung density.

Equation 5, in combination with FIG. 3 illustrates the dependence that sound velocity has on the volumetric fraction of tissue, the volumetric fraction of air, the tissue density and the gas compliance. The tissue compliance and the gas density play essentially no role in the determination of velocity.

Sound velocity in composite materials is determined in part by the product of the tissue density and the gas compliance. The result of this is that the lung parenchyma appears to act like homogeneous mass-loaded air as far as sound propagation is concerned, such that the velocity of sound propagation through the tissue is markedly slower than through air. Substitution of known values for tissue density, $\rho_t$ and gas compliance, $C_g$ in equation 5 gives:

$$v = \frac{11.82}{\sqrt{h(1-h)}} \quad (6)$$

Differentiation of v in equation 6 with respect to h determines a minimum value for velocity at h=0.5 where v=23.6 ms$^{-1}$. For values of h<0.5 the velocity increases with decreasing lung density and conversely for h>0.5 the velocity decreases with decreasing lung density. This is clarified by way of illustration in FIG. 3.

The quadratic properties of equation 6 result in the presence of two values for h for any particular value of measured velocity. These values are:

$$h = 0.5 \pm \sqrt{0.25 - 139.56/v^2} \quad (7)$$

Therefore, the determination as to whether h is above or below 0.5 must be made on physical grounds or by making paired velocity measurements where h is changed between measurements. The direction of the associated change in velocity (increasing or decreasing) can then be used to indicate whether h is above or below 0.5. Therefore, the volumetric fraction of tissue and gas in the lung and hence lung density can be determined directly from measuring the velocity of sound as it propagates through the tissue.

The sound may be introduced in any non-invasive manner, such as by percussion, or using any mechanical, electrical or other transducer which is capable of generating acoustic sounds. It is preferable that the sound which is introduced to the tissue possesses properties which allow it to easily be distinguished from environmental noise which may be present. Examples may include a single tone or a sinusoidal wave. In a preferred embodiment of the invention, a pseudo-random noise is produced by an electro-acoustic transducer and introduced into the tissue. The transducer is preferably attached to the surface of the biological tissue through which sound velocities are being measured. It is preferred that the pseudo-random noise signal which is used has characteristics which are similar to a white noise signal, but with mathematical properties which allow its amplitude to be defined at any moment in time. Furthermore, it is preferred that introduction of the pseudo-random noise signal to the tissue occurs in bursts, preferably of 0.1 to 20 seconds duration, and the sounds are produced preferably with frequencies which range from 20 Hz to 25 kHz and at a sound pressure level of between 1 and 100 Pascal.

The sound can then be recorded at a location spaced from the position at which the sound is introduced, preferably on the surface of the biological tissue which is spatially distinct from the location of the transducer, using a sound detection means such as a microphone or a vibration detector, such as an accelerometer, which has a frequency response that is flat in the acoustic region, preferably between 20 Hz and 25 kHz. It is preferred that there are at least two of these detectors used to measure the sound, wherein one detector is positioned near a sound-generating acoustic transducer, and another is located at a position spaced from the first position of the tissue being assessed. This enables the sound pressure level, phase, and frequency content of the signal which is produced by the acoustic transducer (the input signal) to be accurately defined before it is detected by the spatially separated second detector. Placement of the second detector is preferably substantially in line with the acoustic transducer and the first detector.

The detector or preferably a microphone output may be amplified using low noise isolation amplifiers and band-pass filtered with cut-off frequencies and roll-off characteristics which depend on the acoustic properties of the tissue which is being assessed. For example, for measurements made on the neonatal lung, the pass band is preferably between 50 Hz and 5 KHz with a roll-off which corresponds to that of a 4$^{th}$ order linear phase filter. These filters remove any very low frequency environmental noise (e.g. below 10 Hz) that can adversely affect the performance of auto-scaling amplifiers into which the filtered signal may be fed.

The amplified output signal from the detector or microphone can then be processed by any means necessary, and a cross-correlation analysis of the input and output signals performed.

The cross-correlation function can be calculated using the output of the microphone which is located in close proximity to the acoustic transducer as the input signal, x(t) and the output of the second microphone located on the other side of the tissue as the output signal, y(t) wherein the cross-correlation function can be calculated as $$R_{xy}(\tau) = \lim_{T \to \infty} \frac{1}{T} \int_0^T x(t)y(t+\tau)dt$$

where T is the observation time, and $\tau$ is the delay time between x(t) and y(t) at which $R_{xy}(\tau)$ is calculated.

The impulse response of the system in the time domain can also be determined. It is preferable that the impulse response then undergoes Fast Fourier Transformation so that the signal is transformed into the frequency domain and the transfer function of the tissue can be determined. This transfer function provides a quantitative indication of the characteristics of the tissue, wherein:

(a) the magnitude of the transform provides data relating to the transmission of the sound as it propagates through the tissue as a function of frequency (Rife and Vanderkooy, 1989); and (b) the phase of the transform (after "unwrapping") can be used to calculate the phase difference, time delay and velocity of the sound for each frequency that is present in the psuedo-random noise signal which is introduced to the tissue by the acoustic transducer.

Commercially available acoustic hardware and software packages may be used to generate the psuedo-random noise signal, and to perform initial data processing. External noise which is not introduced to the tissue as part of the psuedo-random noise signal is strongly suppressed by the cross-correlation process thereby improving the quality of the measurements made.

A separate analysis of the relative transmission of the sound through the tissue can be used to identify resonant and anti-resonant frequencies of the tissue which is being assessed. Changes in these frequencies can then be used to assess regional differences in tissue topology which may be related to pathology.

Despite numerous experimental investigations (Kraman 1983, Goncharoff et al. 1989, Wodicka and Shannon 1990) of trans-pulmonary sound transmission where the source of sound is placed at the mouth, there has been no theoretical model which described sound transmission through the thorax. The present invention uses a simple model, based on the double wall transmission model that is used in architectural acoustics (Fahy 1985) to describe the sound attenuating effect of double walls separated by a compliant air layer, as is present in the lung.

Figure 4A:
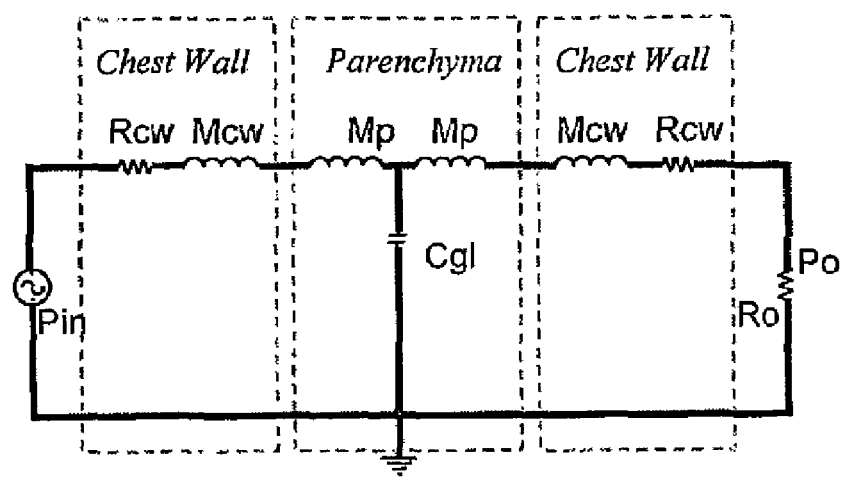
FIG. 4(a) illustrates an electric circuit which models the acoustic characteristics of the thorax.

The essential features of this model as it relates to the thorax can be represented by an electrical equivalent circuit that can be used to describe the pertinent features of sound transmission through the thorax. This model is illustrated in FIG. 4(a). This approach to the analysis of acoustic transmission across the thorax facilitates analysis using sophisticated circuit emulation software such as SPICE to explore the effect of changing model parameters. In the equivalent electric circuit model where:

$R_{cw}$ is the loss component associated with the chest wall and parenchyma;

$M_{cw}$, $M_p$ is the surface mass of the chest wall and parenchyma respectively;

$C_{gl}$ is the lung gas compliance;

$P_{in}$, $P_o$ are the acoustic input and output sound pressure levels respectively; and $R_0$ is the acoustic impedance of free space (414 MKS Rayls).

Figure 4B:
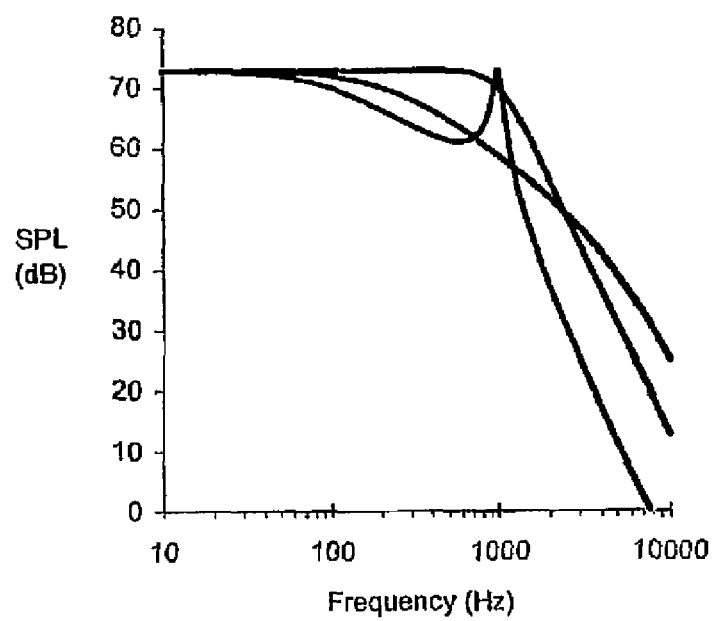
FIG. 4(b) illustrates (1) large, (2) moderate and (3) small acoustic losses as measured using the electric circuit model and which represents the output SPL as would be measured at a chest microphone when the input SPL is 105 dB.

As illustrated in FIG. 4(b), the model can be used to simulate the effect that changing $R_{cw}$ has on the transfer function of the equivalent circuit which represents the chest. This transfer function can be described mathematically as $P_o(f)/P_{in}(f)$ where f is the frequency and $P_{in}(f)$ and $P_o(f)$ are the input (transducer) and output (chest microphone) sound pressure levels (SPL) respectively. As $R_{cw}$ is decreased, the transfer function becomes progressively more peaked or resonant as illustrated by curves 1 to 3 in FIG. 4(b).

At sufficiently high frequencies, the output sound pressure level for all three curves falls asymptotically at a rate of 60 dB per decade. As the frequency is increased above the resonant frequency, the response is dominated by the inertial mass of the proximal and distal chest walls, and the shunt gas compliance of the lung. These act together to produce the 60 dB per decade fall-off, such that the thorax is, in effect, acting like a third order low-pass electrical filter. Analysis of the equivalent circuit, neglecting losses, shows that the resonant frequency of the thorax, $f_0$, can be determined using:

$$f_0 = \frac{1}{2\pi}\sqrt{\frac{2}{C_{gl}(M_{cw}+M_p)}} \tag{8}$$

Furthermore, if the transfer function is measured at $f_0$ and at another frequency well above $f_0$, say, $3f_0$ then using an analysis of the equivalent circuit, an explicit expression for lung gas compliance, $c_{gl}$, can be deduced in the form $$C_{gl} = \frac{4.18 \times 10^{-2} G}{f_0} \tag{9}$$

where $G=|P_o(f)/P_{in}(f)|$ and is the magnitude of the transfer function of the thorax measured at $3f_0$. This equation has been verified using SPICE simulation.

It follows that gas volume $V_{gl}$ can be computed using equation 9:

$$V_{gl}=\gamma P_0 C_{gl} \tag{10}$$

where $\gamma$ is the adiabatic gas constant and $P_0$ is the atmospheric pressure A further important application of this model is illustrated in FIGS. 5(a) and 5(b). FIG. 5(a) shows the experimentally measured thorax transfer function in a preterm infant soon after delivery but before surfactant administration (pre) and after the administration of surfactant (post) (Sheridan 2000). There is a steep fall-off in sound transmission for frequencies above 1000 Hz pre-surfactant and the leftward shift of this fall-off accompanied by an increase in attenuation of 10 dB following surfactant administration. A similar 10 dB change can be simulated in the model by increasing $C_{gl}$ by about a factor of three while maintaining other parameters constant as illustrated in FIG. 5(b). Although a measurement of lung gas compliance was not made during these experiments, and is not feasible using currently available technology, it would be expected that such an increase in compliance (associated with an increase in gas volume) would occur after surfactant administration.

An important component of acoustic transmission which can be modelled using the equivalent electric circuit is the loss component Rcw illustrated in FIG. 4(a) which includes acoustic loss in the chest wall and parenchyma. Because the chest wall is acoustically thin, the dissipative loss in the wall is negligible but the loss in the parenchyma, which includes a large number of serial mass-compliance interfaces formed from the tissue and gas comprising the parenchymal structure, may be considerable. One model that has been proposed to account for acoustic loss in the parenchyma comprises air bubbles in water, for which an analysis already exists. In this model, absorption occurs because acoustic work is required to alternately compress and expand these bubbles.

It has been shown (Wodicka 1989) that the plane wave attenuation produced by N bubbles over distance x is given by:

$$P(x) = P_0 e^{-(\frac{N\sigma}{2})x} \quad (11)$$

where $\sigma = 16\pi^2 r_o^4 \rho_t c_t R/\{R^2 + (\omega M - 1/\omega C)^2\}$
P(x) is the SPL at x
$P_o$ is the SPL at x=0
$r_0$ bubble radius
$c_t$ sound speed in tissue
R, M, C are the effective mechanical resistance, mass and compliance of the bubbles respectively
Attenuation, $$\alpha = \frac{P(x)}{P_0}$$

in dB/cm can then be written as:

$$\alpha = 4.35 N\sigma \quad (12)$$

This is a complex function of R, M, C but a simplified expression for the attenuation can be deduced by recognising that the acoustic vibration of the bubbles (alveoli) is dominated by bubble compliance C at frequencies which are much lower than resonance (ie. <≈10 kHz for realistic alveoli sizes). Therefore, attenuation can be reduced to:

$$\alpha = 2.36 \times 10^{-2} r_0^6 f^3 N \quad (13)$$

The number of bubbles per unit volume N is approximately related to the gas fraction (1−h) by:

$$N = \frac{3(1-h)}{4\pi r_0^3} \quad (14)$$

hence equation 13 can be written as $$\alpha = 1.35 \times 10^{-3} \frac{f^3(1-h)^2}{N} \quad (15)$$

Figure 6:
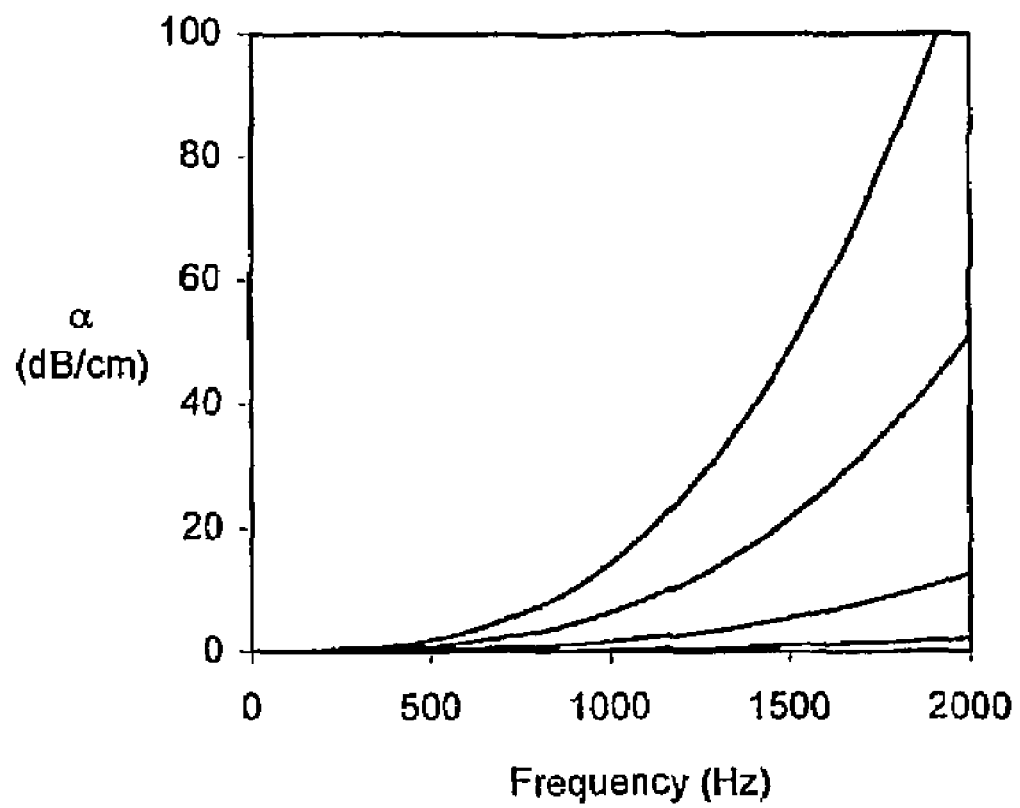
FIG. 6 shows the relationship between frequency and the attenuation coefficient α plotted with tissue fraction h as a parameter.

From these equations, it can be seen that:

(a) absorption is related to the square of the gas fraction (1−h); a small increase in the tissue fraction h is associated with a marked decrease in high frequency attenuation (FIG. 6). This may explain the increased transmission of sound across the chest wall which can be observed clinically at high frequencies, following pneumonic consolidation of the lung; and (b) attenuation is a strong function of both the frequency f and the alveolar radius $r_0$. This may explain, in part, the rapid fall-off in transmitted sound at high frequencies seen in both adult and neonatal subjects. The dependence on bubble radius may explain the reduced transmission through the thorax during emphysema.

Furthermore, these equations indicate that:

(a) absorption is related to the square of the gas fraction (1−h); and (b) Sound transmission attenuation is s strong function of both the frequency and the alveolar radius.

Using these relationships between sound transmission velocity in tissues and the tissue characteristics themselves, it is possible to obtain a workable relationship between acoustic measurements and lung pathology or the pathology or condition of other biological tissues.

This method provides a virtually continuous real-time measurement of tissue characteristics by analysing the velocity and attenuation of a defined sound as it propagates through the tissue. The method is applicable in both adults and infants, and for humans and animals. In particular, the present invention can be used in the determination of respiratory conditions in infants who cannot co-operate with presently available conventional stethoscopic methods of respiratory condition analysis which requires vocal co-operation. It is also useful where the patient is critically ill, is unconscious, or is unable to respond or generate a sound which can be used to determine lung condition.

Figure 8:
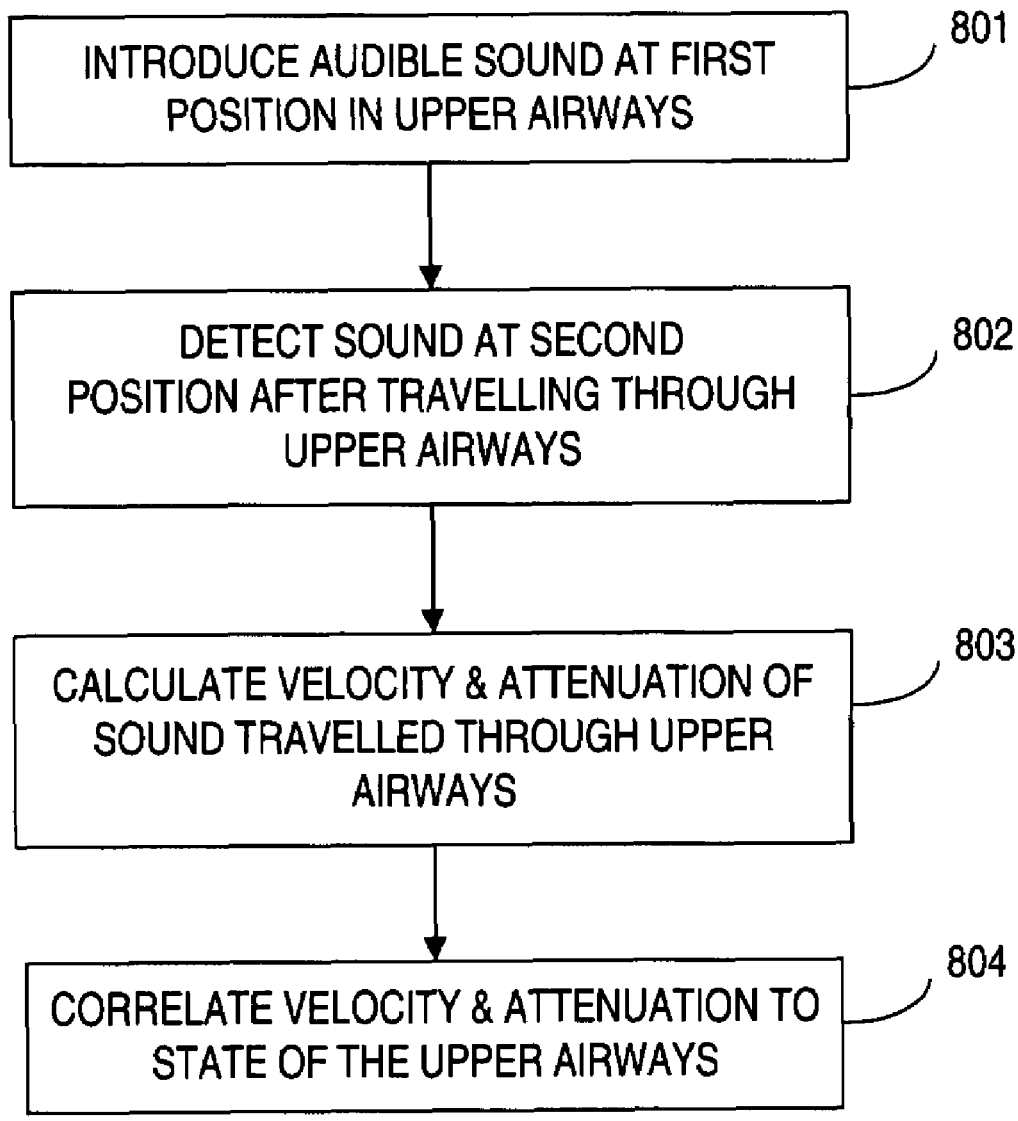
FIG. 8 shows steps of the method where the characteristic being determined is a state of the upper airways in a respiratory tract.

In a preferred aspect of the present invention, the characteristic being determined is a state of the upper airways in a respiratory tract in a patient in situ, and said method, illustrated in FIG. 8, includes:

in a step 801 introducing a sound at first position in the upper airways;

in a step 802, detecting the sound after it has traveled through the upper airways at the second position spaced from the first position;

in a step 803, calculating the velocity and attenuation of the sound traveled through the upper airways from the first position to the second position; and in a step 804, correlating the velocity and attenuation of the sound to the state of the upper airways.

The state of the upper airways may include any condition of the upper airways such as obstructed or open airways. Measurement of the closure or collapse of the upper airway is particularly useful for conditions such as in obstructive sleep apnoea or OSA.

Apnoea, and particularly Obstructive Sleep Apnea (OSA) is associated with closure of the upper airway and lapses in respiration during sleep. Using the present invention, a pseudo-random noise may be introduced into the airway using an acoustic transducer which conducts the sound from a location in the upper airway preferably via a Silastic nosepiece adapter. During normal respiration, the airway is open and the sound is transmitted via the airway to the lung via the trachea, where it subsequently propagates through the lung parenchyma and thorax to the surface of the chest.

A sound-detection device such as a microphone may be attached in the chest region. Variations in the sound level which is measured at the chest region can then be used to model the degree of upper airway patency. The chest region may include the region extending from below the buccal cavity to below the lung.

Preferably, the microphone is placed on the upper chest region generally below the neck and just above the lung.

When the airway is closed, the transmission of sound through the tissue decreases so that it may be undetectable by a microphone located on the chest. Therefore, when the sound falls below a certain value, it is likely to indicate the closure of the airway. When the signal which is detected by a microphone detector or located on the chest region falls below a certain preset limit, an alarm is activated indicating obstruction of the airway. This alarm may wake up the subject which will most often result in the subsequent reopening of the airway, or it may alert attending staff to a patient who is being monitored for OSA or any other airway dysfunction. There are several benefits associated with this method for detecting airway obstruction or closure which include:

(a) the technique is non-invasive;

(b) the technique can be used in new-borns and adults alike, and in humans or in animals;

(c) the technique monitors patency of the airway, not depletion of oxygen or lack of movement as is the case in other apnoea detection devices. As a result of this, the susceptibility of the subject to oxygen depletion is detected before depletion itself occurs, reducing the likelihood of discomfort and tissue damage which can be caused by extended lapses or pauses in regular respiration and oxygen deprivation. This method can also be used to set the optimal level of CPAP to apply to a patient in order to maintain airway patency.

Figure 9:
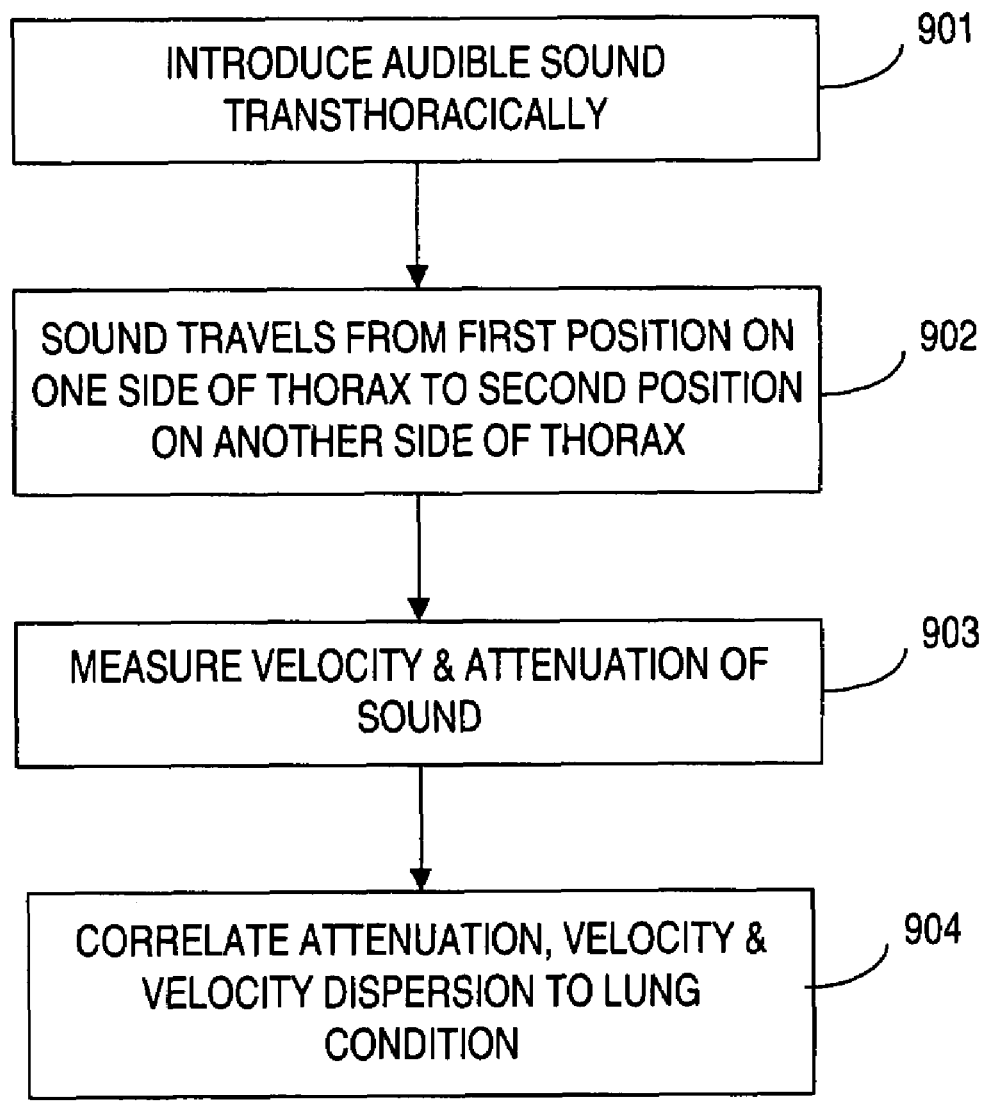
FIG. 9 shows steps of the method, for monitoring lung condition.

In yet another preferred aspect of the present invention, the characteristics are determined for monitoring lung condition in situ said method, illustrated in FIG. 9 comprising:

in a step 901 introducing the audible sound transthoracically so that in a step 902, the sound travels from one side of the thorax, through the lung, to another side of the thorax;

in a step 903, measuring the velocity and attenuation of the sound as it travels from one side of the thorax, through and across the lung, to the other side of the thorax; and in a step 904, correlating the attenuation and sound velocity and velocity dispersion to lung condition.

Previous work shows that measurement of sound velocity alone may provide a technique for assessing lung density and gives an insight into the degree of lung inflation. However, no attempt has been made to evaluate the potential utility of sound velocity and attenuation as a clinical tool.

Lung condition may be selected from the group including but is not limited to:

(a) lung tissue density;

(b) lung gas volume;

(c) regional collapse (atelectasis);

(d) regional blood volume, interstitial oedema; and (e) focal lung pathology such as tumour and global lung disease such as emphysema.

These lung conditions may then be compared with the condition of a normal, healthy lung.

To measure lung condition, the method of the present invention is preferably applied by introducing a sound to the thorax and hence to the lung preferably by applying an acoustic transducer to the thorax on one side of the chest and calculating the sound velocity and attenuation using a detector or microphone which is attached to the other side of the chest and which detects the transmitted sound. Previous measurements of lung condition or volume have been made by introducing sound to the lung tissue via the trachea. However, there are problems associated with this method for the lung which result from the unknown distance between the trachea and chest wall, and an inability to selectively distinguish the effects of the airway from the effects of the lung parenchyma on the velocity of the introduced sound. In other measurement techniques, the sound is generated by the subject by respiration, coughing or speech, or is introduced through percussion. However, this presents a key limitation because the acoustic properties of these sounds are subject-dependent and beyond control, particularly in the newborn infant, who is unable to reliably produce the desired sound on command.

The present invention exhibits a novel approach to examining the acoustic properties of the biological tissues, including the upper airways and of the thorax, by introducing sounds with a known and precisely defined spectral content as the investigative tool. For the lung, by utilising this sound which is introduced directly to the wall of the thorax, and by recording the sound after it is transmitted across the thorax, uncertainties associated with noise introduced via the trachea are eliminated. Without being restricted by the theory, research suggests that the lung tissue type which is primarily responsible for changes in sound velocity as it propagates through the thorax is the lung parenchyma; the contribution to changes in sound wave velocity and attenuation which is made by the airways is insignificant.

Many lung diseases are associated with characteristic features that can be detected using auscultation of the chest (Lowe and Robinson, 1970). In the normal lung, frequencies above 300-400 Hz are heavily attenuated by thoracic tissue, and on auscultation, respiration sounds are soft, conversational sounds are muffled, and whispered sounds are inaudible. By contrast, pneumonic consolidation greatly reduces the attenuation of high frequency sounds, resulting in characteristic respiration sounds known as 'bronchial breathing' and strong transmission of whispered (high-frequency) sounds known as 'whispering pectriloquy'. A pleural effusion on the other hand, classically gives rise to increased attenuation of low frequency sound, causing vocal sounds to have a high pitched nasal quality known as 'aegophony'.

Studies have been published which examine the effect of lung condition on sound attenuation in the healthy human lung. However, these studies have failed to measure the effect of lung inflation on sound attenuation. The present invention utilises transthoracically introduced sound and preferably measures the sound velocity and sound attenuation to determine lung condition. Lung conditions assessed using the present invention may include lung density and lung volume. However, other lung conditions may be determined by correlating changes in sound velocity and sound attenuation which are associated with known lung conditions with sound velocities and attenuation which are measured using a normal, healthy lung.

Tissue density may be measured using sound velocity alone. However, sound attenuation may also be introduced as a parameter for the determination of tissue density. Tissue density may be a measure of the amount of fluid or blood in the tissue. In the lung, it may also indicate gas volume, regional collapse (atelectasis), regional blood volume, interstitial oedema and both focal lung disease (eg tumour) and global lung disease (eg emphysema) which may be compared with a normal, healthy lung.

Figure 10:
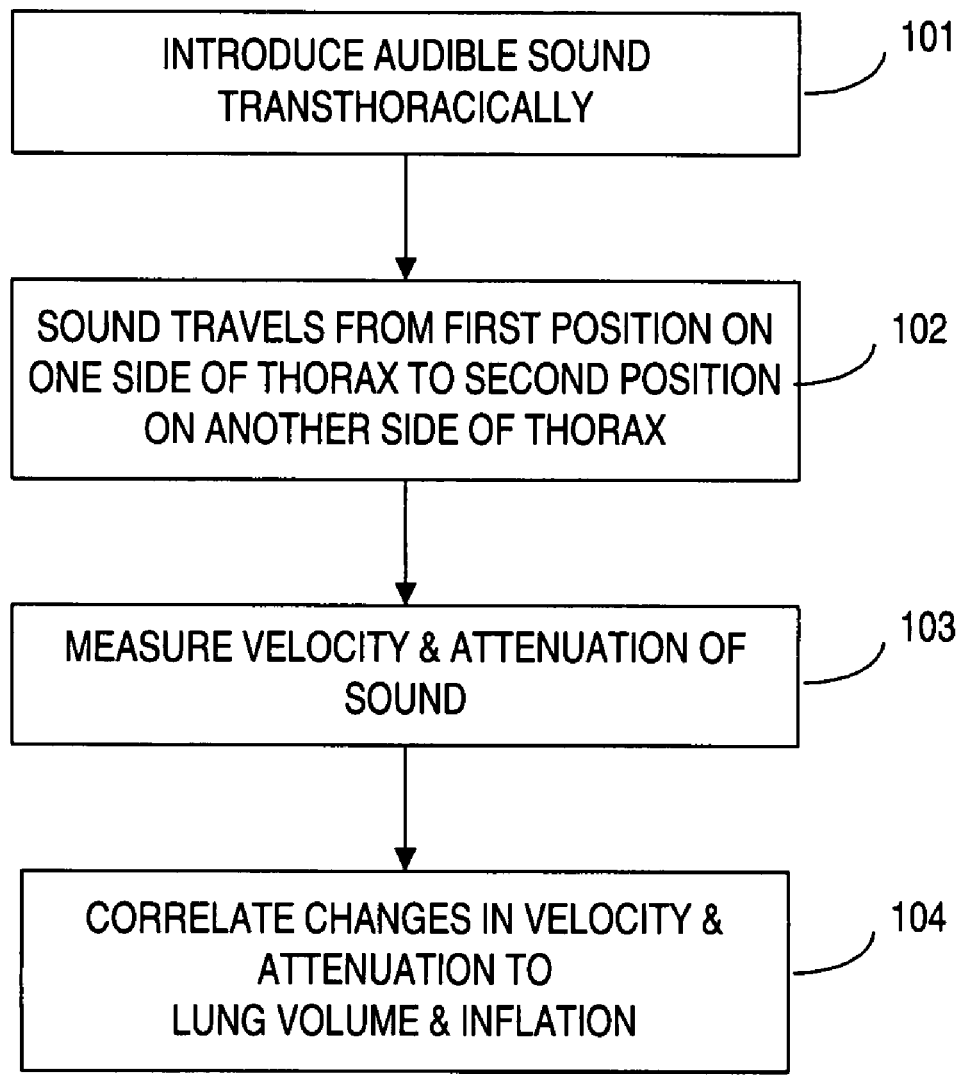
FIG. 10 shows steps of the method, for measuring lung inflation.

In yet another preferred aspect of the present invention of the characteristics are determined for measuring lung inflation, said method, illustrated in FIG. 10, including:
- in a step 101, introducing the audible sound transthoracically so that the sound travels, in a step 102, from one side of the thorax, through the lung, to another side of the thorax;
- in a step 103, measuring the velocity and attenuation of the sound as it travels from one side of the thorax, through and across the lung, to the other side of the thorax; and
- in a step 104, correlating changes in sound velocity and attenuation with lung volume and inflation.

Lung gas volume is inversely proportional to lung density and may be measured using sound velocity and preferably sound attenuation. Furthermore, measurement of the velocity of a sound as it propagates from one side of the thorax through the lung tissue to the other side of the thorax can be correlated with a change in lung volume (inflation). This may be done in isolation, or during or after clinical interventions which alter the degree of lung inflation. Measurements taken may include:
a) before and at intervals after treatment with surfactant;
b) before and at intervals after commencement of Continuous Positive Airway Pressure (CPAP) to recruit lung volume in the presence of hyaline membrane disease and/or atelectasis;
c) before and at intervals after the commencement of mechanical ventilation; and
d) before and immediately after endotracheal tube suctioning.

The degree of change in the sound velocity and preferably also of sound attenuation may be used together to provide a more conclusive indication of the degree to which the lung is inflated. Lung inflation may be determined using a single measurement, or it may be determined continuously, thereby enabling the monitoring of progress of lung disease and its treatment. This has particular value in the treatment and monitoring of lung disorders in premature babies over a period of time.

Figure 11:
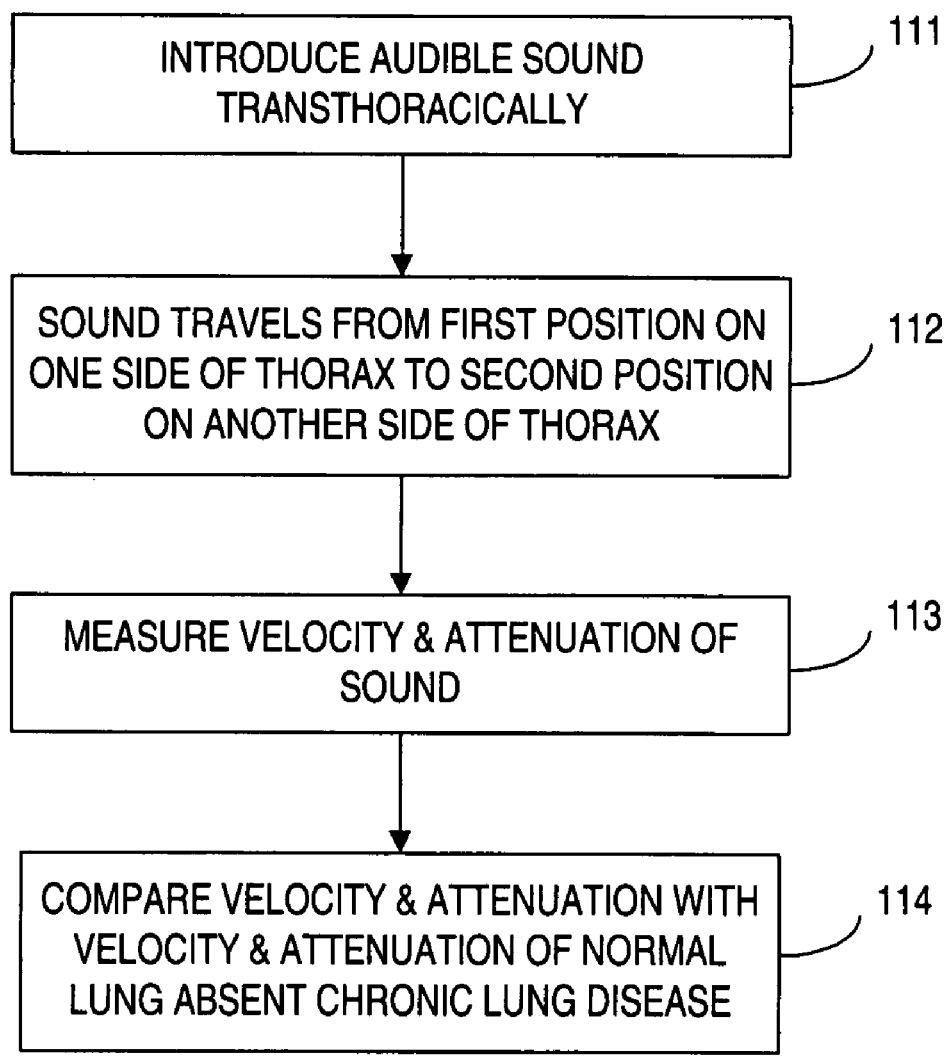
FIG. 11 shows steps of the method, for predicting chronic lung disease in infants.

In yet another preferred aspect of the present invention, of the characteristics are determined for predicting chronic lung disease in infants said method, illustrated in FIG. 11, including:
- in a step 111 introducing an audible sound transthoracically so that the sound travels, in a step 112, from one side of the thorax, through the lung, to another side of the thorax;
- in a step 113, measuring the velocity and attenuation of the sound as it travels from one side of the thorax, through and across the lung, to the other side of the thorax; and
- in a step 114, comparing the measured sound velocity and attenuation with that of a normal lung in the absence of chronic lung disease.

Abnormal lung density due to over- or under-inflation of the lung may be associated with increased lung injury and the propensity for development of chronic lung disease in infants. Therefore, measurements of sound velocity and attenuation (which relate to lung density) in a premature infant may allow inflation to be optimised and risk of chronic lung disease to be reduced.

Measurements of the sound velocity and sound attenuation may be made on days 1, 2, 3, 5, 7, 10 and 14 or any interval thereof and then at weekly intervals until about 36 weeks. As a comparison, and to complement measurements made using the present invention, absolute lung volume may be measured using the gold-standard and long-established helium dilution technique at the time of the acoustic measurements. Results taken from infants who subsequently develop chronic lung disease (defined either as oxygen dependency at 28 days or at a postmenstrual age of 36 weeks) may be compared with results from those who do not.

Figure 12:
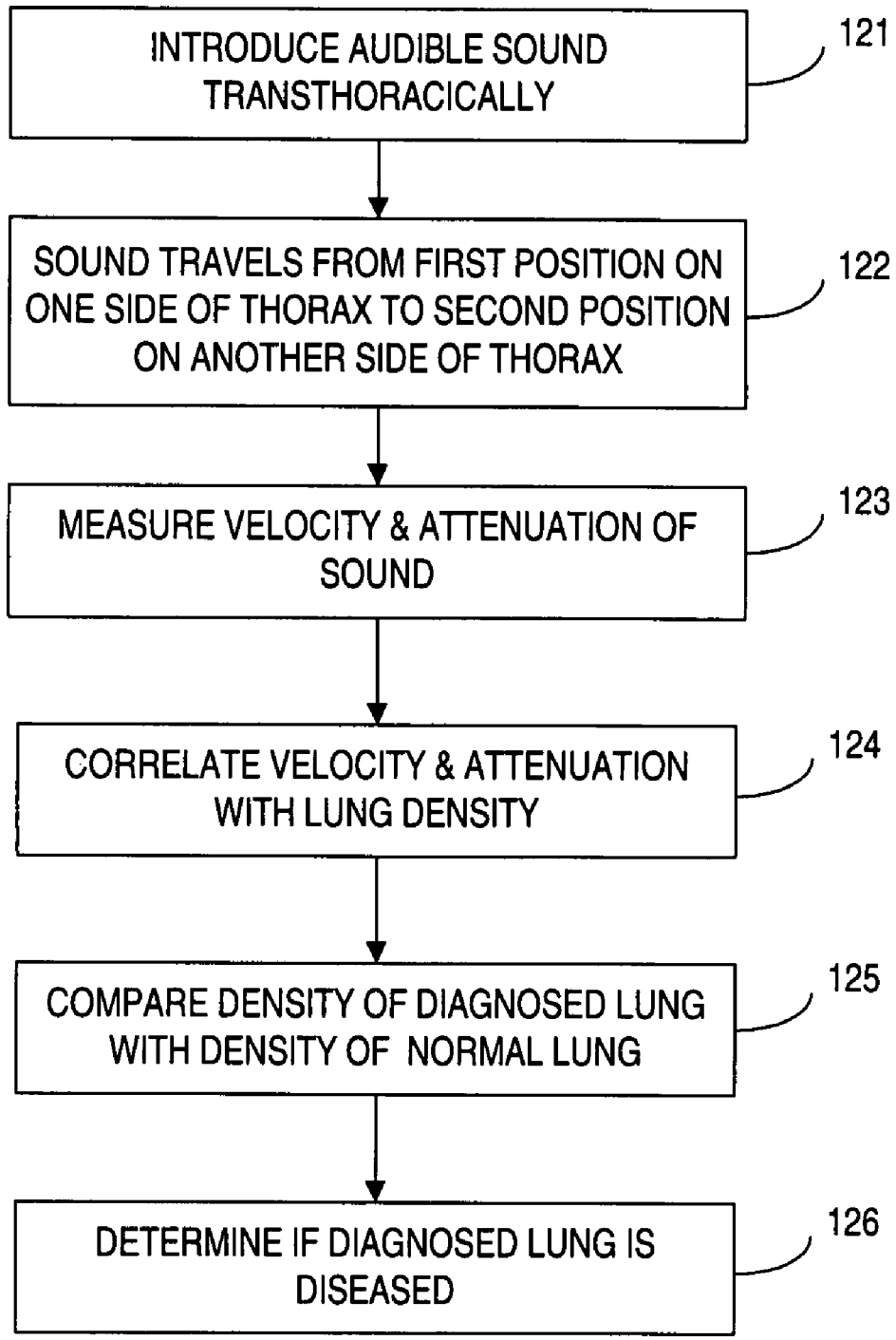
FIG. 12 shows steps of the method, for diagnosing lung disease.

In yet another preferred aspect of the invention the characteristics are determined for diagnosing lung disease, said method, illustrated in FIG. 12, and including measuring lung density and further including:
- in a step 121, introducing the audible sound transthoracically so that the sound travels, in a step 122, from one side of the thorax, through the lung, to another side of the thorax;
- in a step 123, measuring the velocity and attenuation of the sound as it travels from one side of the thorax, through and across the lung, to the other side of the thorax; and
- in a step 124, correlating sound velocity and attenuation with lung density and in a step 125, comparing the density of the lung being diagnosed with the density of a normal lung to determine, in a step 126, if the lung being diagnosed is diseased.

A similar technique can be used to assist in diagnosing lung disease wherein again, a sound is introduced to the thorax such that it travels from one side of the thorax, through the lung, to another side of the thorax. The sound velocity and preferably attenuation which is measured is then compared with that of a normal, healthy lung. Since lung disease often manifests in reduced lung volume, a comparison can be used, again, to provide an indication as to whether a subject's lung exhibits a propensity for lung disease. Common lung diseases may include emphysema, asthma, regional collapse (atelectasis), interstitial oedema and both focal lung disease (e.g. tumour) and global lung disease (e.g. emphysema). Each of these may be detectable when measurements of the velocity and attenuation of a sound which is transmitted through a diseased lung is compared with that of a lung in normal condition.

Figure 13:
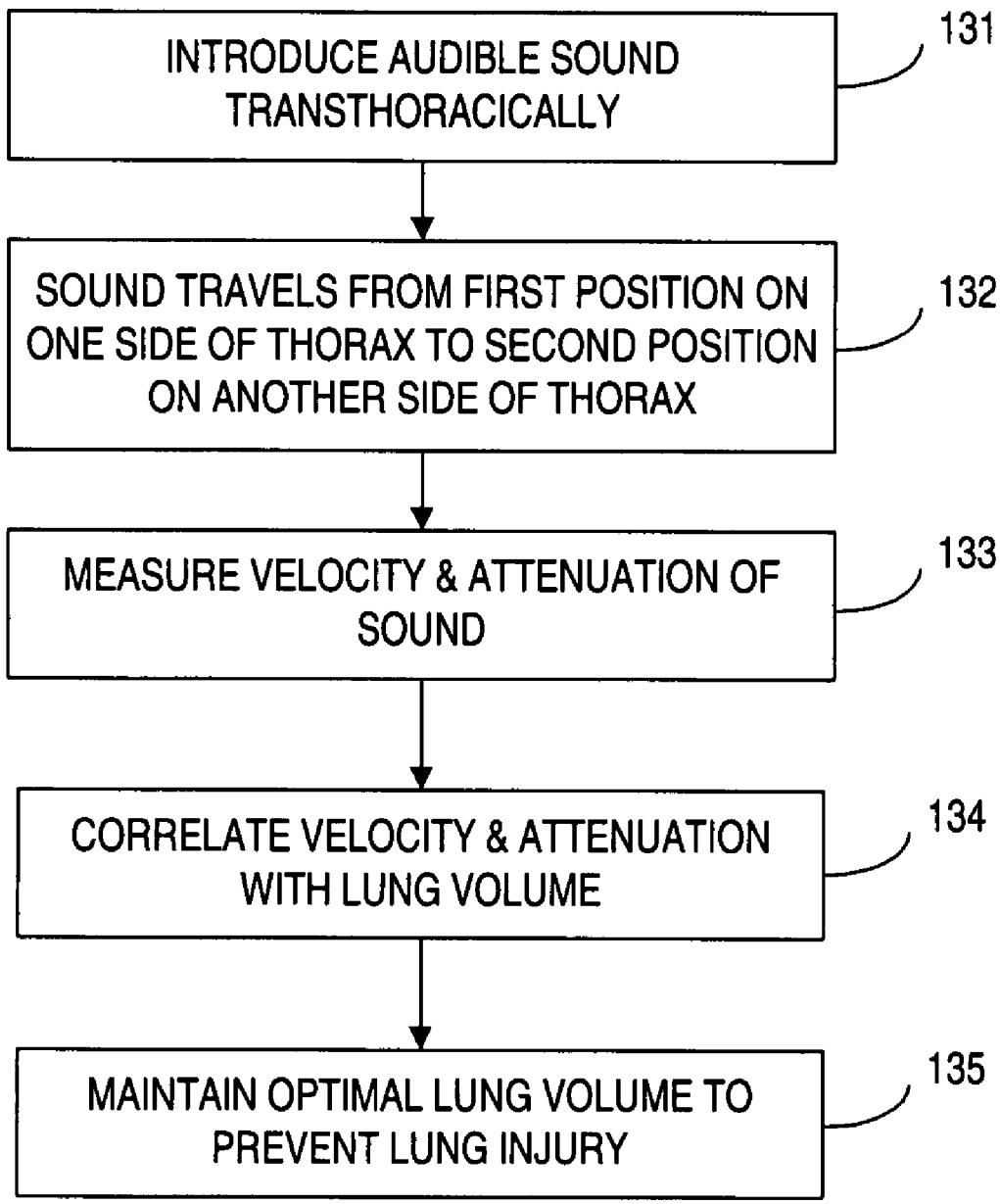
FIG. 13 shows steps of the method, for preventing lung injury.

In yet another preferred aspect of the present invention, of the characteristics are determined for preventing lung injury, said method illustrated in FIG. 13, including monitoring lung condition by:
- in a step 131, introducing the audible sound transthoracically so that the sound travels, in a step 132, from one side of the thorax, through the lung, to another side of the thorax;
- in a step 133, measuring the velocity and attenuation of the sound as it travels from one side of the thorax, through and across the lung, to the other side of the thorax;
- in a step 134, correlating the sound velocity and attenuation with lung volume; and
- in a step 135, maintaining a lung volume at an optimal volume such that the lung is substantially free of atelectasis or over-inflation (volutrauma).

Figure 1:
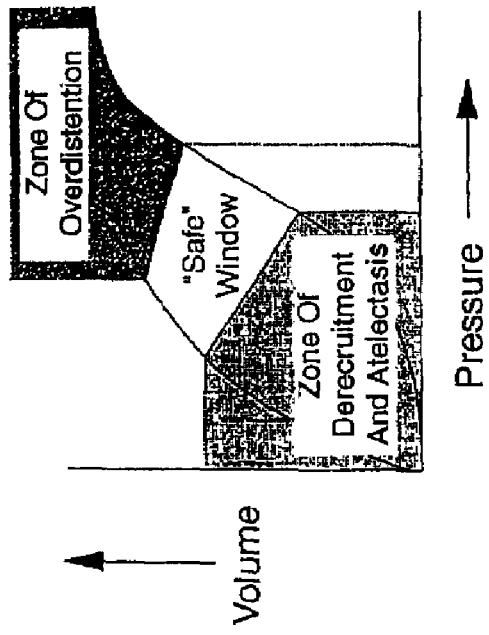
FIG. 1 shows a pressure-volume curve of a moderately diseased lung illustrating two hazardous regions of lung volume, and indicating an optimal "safe" window there between (from Froese, 1997).

The present invention provides a reliable method for monitoring lung density and volume in situ. However, it can also be used to provide a method of preventing lung injury by again, introducing a sound transthoracically so that the sound travels from one side of the thorax through the lung to another side of the thorax. The velocity of the sound can be measured as it travels from one side of the thorax through the lung to the other side of the thorax, and the measurement can be used to indicate the volume of the lung which can then be used in the maintenance of an optimal lung volume which is substantially free of atelectasis or over-inflation (volutrauma). These optimal lung volumes are illustrated graphically in FIG. 1, wherein there exists a window inside which the possibility of causing lung injury can be minimised. This window is framed by under-inflation and over-inflation lung volumes. If lung volume is maintained inside this window, the likelihood of lung injury will be reduced. However, to ensure the volume does not rise excessively and does not drop to the level of atelectasis, it is necessary to constantly monitor the lung's volume.

In another aspect of the present invention there is provided an apparatus for determining characteristics of biological tissues, the apparatus including:
- a sound generating device which generates a sound;
- a recording device which records the sound after it has traveled from one position of the biological tissue, through the tissue and to another position of the tissue;
- an analysis device which calculates the velocity and attenuation with which the sound travels through the tissue, and which can preferably perform spectral analysis on the data recorded.

In yet another preferred aspect of the present invention, there is provided an apparatus for monitoring lung condition, said apparatus including:
- a sound generating means to generate a sound transthoracically so that the sound travels from one side of the thorax, through the lung, to another side of the thorax;
- a recording means to record the sound after it has traveled from one side of the thorax, through and across the lung, to the other side of the thorax;
- an analysis device which calculates the attenuation and velocity with which the sound travels from one side of the thorax, through and across the lung, to the other side of the thorax, and which can preferably perform spectral analysis on the data recorded.

The present invention can be used to provide a monitoring system which measures sound velocity and preferably combines sound velocity data with measurements of sound attenuation in order to determine the level of lung inflation in a subject. Spectral analysis of the impulse response can indicate frequency components in the sound signal which are more prominent than others and which may be an indicator of pathological or abnormal tissue. Preferably the lung condition is monitored by an independent measure of lung density or lung volume.

The benefits associated with the application and detection of acoustic signals to biological tissues is not limited to the lungs, airways and other tissues associated with respiration. The present invention can be used to detect densities of other porous structures and composite biological tissues which have high or low densities, wherein the ratio of solid to porous tissue gives rise to the change in velocity and sound attenuation which is measured.

The present invention will be more fully described with reference to the accompanying examples and figures. It is to be understood that the description following is illustrative only and should not be taken to be limiting in any way, or as a restriction on the generality of applications for the invention previously described.

REFERENCES

Australian and New Zealand Neonatal Network. Annual Report, 1996-1997.

Baumer J H. International randomised controlled trial of patient triggered ventilation in neonatal respiratory distress syndrome. Arch Dis Child 82: F5-F10, 2000.

Bernstein G, Mannino F L, Heldt G P, Callahan J D, Bull D H, Sola A, Ariagno R L, Hoffman G L, Frantz I D $3^{rd}$, Troche B I, Roberts J L, Dela Cruz T V, and Costa E. Randomized multicenter trial comparing synchronized and conventional intermittent mandatory ventilation in neonates. J Pediatr 128: 453-63, 1996.

Dreyfuss D, Basset G, Soler P and Saumon G. Intermittent positive-pressure hyperventilation with high inflation pressures produces pulmonary microvascular injury in rats. Am Rev Resp Dis 132: 880-884, 1985.

Fahy, F. (1985) Sound and Structural Vibration. Radiation, Transmission and Response. London: Academic Press.

Froese A B. Role of lung volume in lung injury: HFO in the atelectasis-prone lung. Acta Anaesthesiol Scand Suppl 90:126-130, 1989.

Froese A B. High frequency oscillatory ventilation for adult respiratory distress syndrome: Let's get it right this time! Crit Cae Med 25: 906-908, 1997

Gerstmann D R, Minton S D, Stoddard R A, Meredith K S, Monaco F, Bertrand J M, Battisti O, Langhendries J P, Francois A and Clark R H. The Provo multicenter early high-frequency oscillatory ventilation trial: improved pulmonary and clinical outcome in respiratory distress syndrome Pediatrics. 98: 1044-1057, 1996.

Goncharoff, V., Jacobs, J E, and Cugell, D W Wideband acoustic transmission of human lungs. *Med. Biol. Eng. Comp.* 27:513-519,1989.

HIFI Study Group. High frequency oscillatory ventilation compared with conventional mechanical ventilation in the management of respiratory failure in preterm infants. N Engl J Med 320: 88-93,1989.

Jobe A. Pulmonary surfactant therapy. N Engl J Med 328: 861-864,1993.

Kraman, S. S. Speed of low-frequency sound through lungs of normal men. J. Appl. Physiol. 55:1862-1867, 1983.

Lowe R D and Robinson B F. A physiological approach to clinical methods. Churchill, London, 1970.

McCulloch, P R, Forkert P G and Froese A B. Lung volume maintenance prevents lung injury during high-frequency oscillatory ventilation in surfactant-deficient rabbits. Am Rev Respir Dis 137: 1185-1192,1988.

Northway H Q, Rosen R C and Porter D Y. Pulmonary disease following respiratory therapy of hyaline membrane disease. N Engl J Med 276: 357-368, 1967.

Rice, D. A. (1983) Sound speed in pulmonary parenchyma. J. Appl. Physiol. 54:304-308.

Rife D D & Vanderkooy J. Transfer function measurement with maximum length sequences. J Audio Eng Soc 37: 419-444, 1989.

Sheridan, B (2000) Acoustic evaluation of lung inflation in the preterm infant. B. Med. Sci. Thesis, RCBHR, Monash University.

Taghizadeh A & Reynolds E O R. Pathogenesis of bronchopulmonary dysplasia following hyaline membrane disease. Am J Pathol 82: 241-264,1976.

Wodicka, G. R. and Shannon, D. C. Transfer function of sound transmission in subglottal human respiratory system at low frequencies. J. Appl. Physiol. 69(6):2126-2130, 1990.

Wodicka G R, Stevens, K N, Golub, H L, Cravalho, E G and Shannon, D. C. A model of acoustic transmission in the respiratory system. IEEE Ttrans Biomed. Eng. 36: 925-934,1989.

EXAMPLES

Example 1

Measurement of Lung Volume in Adults

Figure 2:
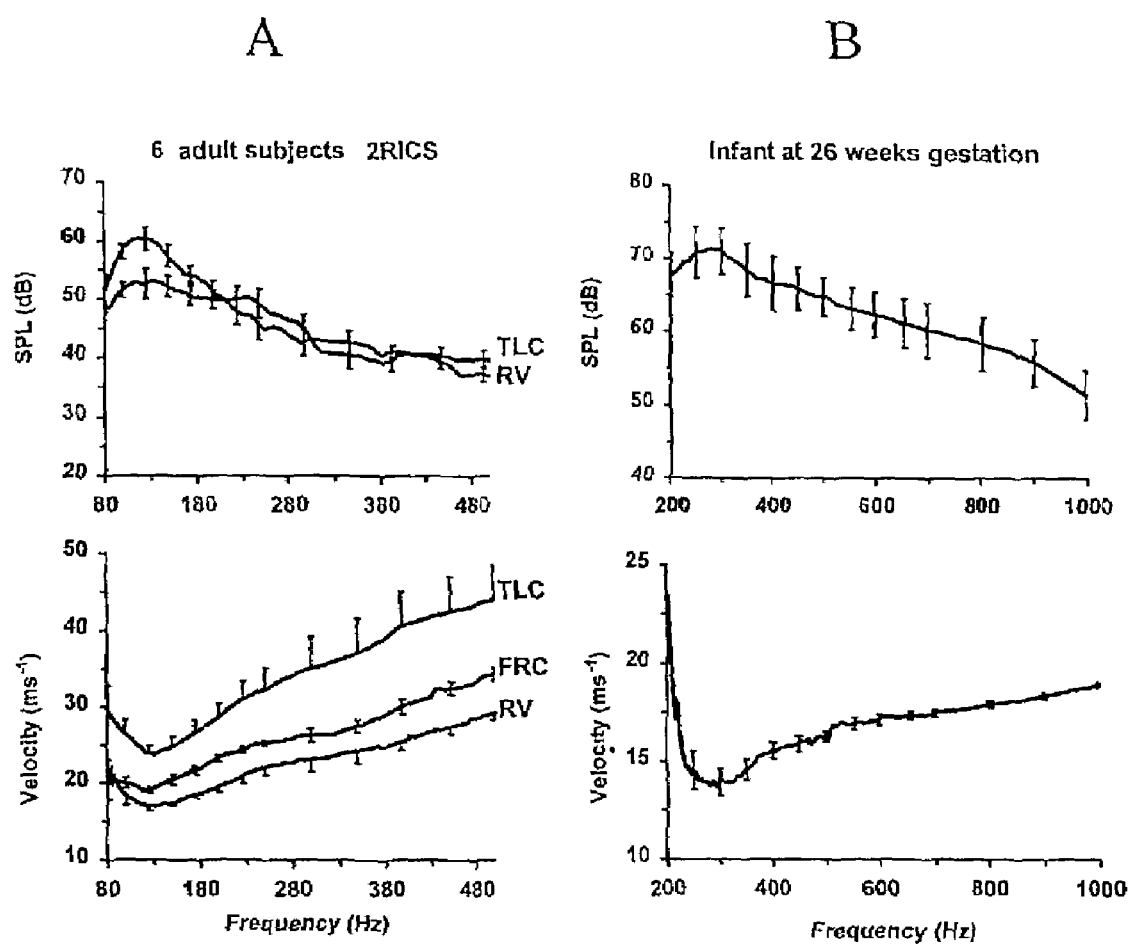
FIG. 2 shows (A) Sound pressure level (dB) and sound velocity (m/s) versus frequency (Hz) for pooled results taken from 5 adult subjects during breath-holds at residual volume (RV), functional residual capacity (FRC) and total lung capacity (TLC). (B) shows results from an infant of 26 weeks gestation with healthy lungs, each data point representing the pooled mean ±S.E. of 5 measurements. The results were obtained from a reference position in the adult with the transducer at the $2^{nd}$ right intercostal space on the anterior chest wall and in the newborn over the right upper chest. In both adult and infant, the microphone was placed on the opposite wall of the chest directly in line with the transducer.

In 5 healthy adult subjects, the velocity and attenuation of sound which was transmitted from one side of the chest to another, in a range of frequencies from 50-1000 Hz was measured at a number of defined positions on the chest. These measurements were taken while the lung volume was varied between Residual Volume (RV) and Total Lung Capacity (TLC). A reference position was established over the right upper zone of the chest. Using this position, a region in the frequency spectrum (around 100-125 Hz) where sound attenuation was much reduced and where the degree of attenuation was directly related to lung inflation (see FIG. 2A, upper panel) was found. The difference in attenuation between RV and TLC was approximately 7.5 dB and statistically significant (P=0.028). Further, it was found that sound velocity was low, averaging around 30 m/sec, and it showed a clear and strong sensitivity to the degree of lung inflation, being appreciably faster at TLC than at RV (FIG. 2A, lower panel). In this study evidence was found which indicated that the effect of inflation on velocity and attenuation varies at different locations in the thorax, particularly in the lower zones. It is likely that this is, in part, attributable to the location of the heart and liver (at RV) in the sound path.

The method of analysis permits determination of phase shift, and therefore velocity as a function of frequency. This work has shown that the speed of sound in the lung parenchyma is dispersive, or frequency dependent, over the range of frequencies studied. This is of considerable importance, since it is theorised that the relationship between velocity and frequency is dependent on regional compliance and inertial (ie mass dependent) properties of the lung. These properties may provide valuable information about the lung since they are partly determined by the condition of the alveolar septum, the degree of fluid infiltration of the lung parenchyma, and the extent of atelectasis.

Preliminary pilot data were collected from newborn infants in the neonatal intensive care unit. FIG. 2B represents a sample result from an infant of 26 wks gestation with healthy lungs, illustrating that measurements can be made using the present invention with a subject who cannot co-operate and who must be studied in the noisy intensive care setting. Interestingly, the frequency region over which sound attenuation is least in the newborn is higher (approximately 300 Hz) than in the adult. In addition, although the relationship between velocity and frequency has a nadir at about 300 Hz compared with 125 Hz in the adult, the dispersive nature of sound velocity which is evident in the adult is also present in the infant.

Example 2

Measurement of Lung Density in Rabbits

Experiments were conducted in 1-2 kg New Zealand white rabbits. These animals were chosen for their similarity in size to the human newborn and their widespread use as a model of neonatal surfactant deficiency. Animals were anaesthetised with intravenous thiopentone, before performing a tracheostomy during which a 3 mm endotracheal tube was inserted into the airway to allow ventilation using a conventional neonatal ventilator (Bournes BP200). Maintenance anaesthesia was be achieved with intravenous fentanyl. The chest was shaved and a microphone and transducer secured in various pre-defined positions, including a reference position over the right upper chest. The animal was then placed in a whole body plethysmograph to monitor absolute lung gas volume at intervals throughout the experiment. Tidal volume was monitored continuously with a pneumotachograph attached to the tracheostomy tube. The sound velocity and attenuation was determined at each location of the where a microphone was situated, and each observation. was the average of 10 repeated measures.

The effect of changes in lung density as a result of lung disease on sound velocity and attenuation was examined by comparing results from 3 groups of rabbits with differing lung conditions:

Group 1—Normal lungs (n=10)
Group 2—Lungs rendered surfactant deficient by saline lavage (n=10)
Group 3—Lungs rendered oedematous by inflation of a left atrial balloon catheter (n=10).

Within each group of animals the effect of changes in lung density, resulting from changes in degree of lung inflation, was examined by making measurements under dynamic and static conditions.

(1) Dynamic measurements during mechanical ventilation. Sound velocity and attenuation may be measured during mechanical ventilation at various levels of positive end-expiratory pressure (PEEP) including 0, 5, 10, 15 and 20 $cmH_2O$. Absolute lung volume at end expiration, and tidal volume may be determined for each level of PEEP. A wide range of PEEP can be employed to ensure that observations are made over a wide range of lung volumes, from under-inflation to over-inflation and including optimal inflation.

(2) Static measurements during apnoea. Sound velocity and attenuation was measured while the lung was transiently held at constant volume after spontaneous respiratory effort had been suppressed by a brief period of hyperventilation. Various lung volumes from below functional residual capacity (FRC) to TLC were achieved by varying airway pressure between −10 and +30 $cmH_2O$. Studying the lung under static conditions allows observations to be made at the extremes of lung volume. These results were directly comparable to observations during breath-hold in adult subjects and enables verification of the cross-correlation technique used in the present invention which increases the system's robusticity against interference from breath sounds.

(3) Static measurements post-mortem. At the completion of (2) above, a lethal dose of anaesthetic was administered and observations of sound velocity and attenuation were repeated across the same range of lung volumes as in (2). The trachea was then clamped at an inflation pressure of 10 $cmH_2O$ before dissecting the lungs so that they were free from the chest and so that their weight and density could be determined. In order to address the question of the regional differences in sound velocity and attenuation observed in the adult human study, final measurements were made of the acoustic properties of the excised lung at the same levels as those studied in the intact thorax. An important aspect of this analysis is that it allowed comparison of results obtained before and after death to establish whether the cross-correlation technique used is resistant to interference from cardiac sounds.

Example 3

Measurement of Lung Inflation in Infants

To be a valuable clinical tool, measurements of sound velocity and attenuation must be sensitive to changes in lung inflation that are of a clinically relevant magnitude. A test of whether measurable changes in sound velocity and attenuation which occurred after clinical interventions which were confidently predicted alter the degree of lung inflation was conducted. It was found that clinical interventions which cause a significant change in lung inflation are associated with changes in sound transmission and velocity which are measurable using the present invention.

Example 4

Prediction of Chronic Lung Disease

It is also necessary to determine whether evidence from acoustic measurements of abnormal lung density are indicative of either under-inflation or over-inflation, and associated with development of chronic lung disease as a result. It was found that abnormal lung density in the first few days of life was more common in infants who subsequently developed chronic lung disease than in those who did not. Serial measurements of sound velocity and attenuation in a population of pre-term infants (n=30) who, by virtue of their gestation (<30 weeks), are at high risk of developing chronic lung disease were made. In this population and using the present invention, it was estimated that about 65% of the population will still be oxygen dependent at 28 days of age, and about 30% will still be oxygen dependent at a postmenstrual age of 36 weeks.

Finally it is to be understood that various other modifications and/or alterations may be made without departing from the spirit of the present invention as outlined herein.

The invention claimed is:

1. A method of determining characteristics of tissue of the respiratory system in situ, said method including:
   introducing an audible sound to the tissue at a first position;
   detecting the sound at a second position spaced from the first position after it has traveled through the tissue;
   calculating the velocity and attenuation of sound that has traveled through the tissue from the first position to the second position; and
   correlating the velocity and attenuation of the detected sound to characteristics of the tissue of the respiratory system.

2. A method according to claim 1 wherein the characteristics include any one of make-up of tissue, volume, condition or position in the body.

3. A method according to claim 1 wherein the tissue of the respiratory system is selected from the group including lung tissue or tissues of the upper airway.

4. A method according to claim 1 wherein the audible sound is produced with frequencies in the range of 20 Hz to 25 kHz.

5. A method according to claim 1 wherein the sound is produced at a sound pressure level between 1 and 100 Pascal.

6. A method according to claim 1 wherein the sound is detected by a sound detector means including a microphone or a vibration detector having a frequency response that is flat in the acoustic region.

7. A method according to claim 6 wherein the frequency response that is flat in the acoustic region is between 20 Hz and 25 kHz.

8. A method according to claim 1 wherein a characteristic being determined is a state of the upper airways in a respiratory tract in a patient in situ, and wherein:
   the first position is in the upper airways;
   the sound is detected at the second position after it has traveled through the upper airways;
   the calculated velocity and attenuation is of the sound that has traveled through the upper airways; and
   the velocity and attenuation of the sound is correlated to a characteristic being the state of the upper airways.

9. A method according to claim 8 wherein the state of the upper airways is determined as an obstructed or open airway.

10. A method according to claim 8 wherein the state of the upper airways is determined to monitor obstructive sleep apnoea and wherein a change in the velocity and attenuation of the sound indicates a change in the state of the upper airway.

11. A method according to claim 8 wherein the first position in the upper airways is in the nasal region and the second position spaced from the first position is in the upper chest region below the neck and above the lung.

12. A method according to claim 1 wherein the characteristics are determined for monitoring lung condition in situ, and wherein:
   the audible sound is introduced transthoracically so that the sound travels from the first position on one side of the thorax, through the lung, to the second position on another side of the thorax;
   the calculating step includes measuring the velocity and attenuation of the sound as it travels from one side of the thorax, through and across the lung, to the second position the other side of the thorax; and
   the attenuation, the sound velocity and velocity dispersion are correlated to a characteristic being lung condition.

13. A method according to claim 12 wherein the lung condition is selected from the group including:
   (a) lung tissue density;
   (b) lung gas volume;
   (c) regional collapse (atelectasis);
   (d) regional blood volume, interstitial oedema; and
   (e) focal lung pathology including tumour and global lung disease.

14. A method according to claim 1 wherein the characteristics are determined for measuring lung inflation, and wherein:
   the audible sound is introduced transthoracically so that the sound travels from the first position on one side of the thorax, through the lung, to the second position on another side of the thorax;
   the calculating step includes measuring the velocity and attenuation of the sound as it travels from one side of the thorax, through and across the lung, to the other side of the thorax; and
   changes in sound velocity and attenuation are correlated with characteristics being lung volume and inflation.

15. A method according to claim 1 wherein the characteristics are determined for predicting chronic lung disease in infants and wherein:

the audible sound is introduced transthoracically so that the sound travels from the first position on one side of the thorax, through the lung, to the second position on another side of the thorax;

the calculating step includes measuring the velocity and attenuation of the sound as it travels from one side of the thorax, through and across the lung, to the other side of the thorax; and the correlating step includes comparing the measured sound velocity and attenuation with that of a normal lung in the absence of chronic lung disease.

16. A method according to claim 1 wherein the characteristics are determined for diagnosing lung disease, said method including measuring lung density and wherein:

the audible sound is introduced transthoracically so that the sound travels from the first position on one side of the thorax, through the lung, to the second position on another side of the thorax;

the calculating step includes measuring the velocity and attenuation of the sound as it travels from one side of the thorax, through and across the lung, to the other side of the thorax; and the correlating step includes correlating sound velocity and attenuation with a characteristic being lung density and comparing the density of the lung being diagnosed with the density of a normal lung to determine if the lung being diagnosed is diseased.

17. A method according to claim 16 wherein the lung disease is selected from the group including emphysema, asthma, regional collapse (atelectasis), interstitial oedema, focal lung disease and global lung disease.

18. A method according to claim 1 wherein the characteristics are determined for preventing lung injury, said method including monitoring lung condition wherein:

the audible sound is introduced transthoracically so that the sound travels from the first position on one side of the thorax, through the lung, to the second position another side of the thorax;

the calculating step includes measuring the velocity and attenuation of the sound as it travels from one side of the thorax, through and across the lung, to the other side of the thorax;

the correlating step includes correlating the sound velocity and attenuation with a characteristic being lung volume; and the method further includes the step of:

maintaining a lung volume at an optimal volume such that the lung is substantially free of atelectasis or overinflation (volutrauma).

* * * * *